United States Patent
Podhajsky et al.

(10) Patent No.: US 8,211,100 B2
(45) Date of Patent: *Jul. 3, 2012

(54) ENERGY DELIVERY ALGORITHM FOR MEDICAL DEVICES BASED ON MAINTAINING A FIXED POSITION ON A TISSUE ELECTRICAL CONDUCTIVITY V. TEMPERATURE CURVE

(75) Inventors: Ronald J. Podhajsky, Boulder, CO (US); Kristin D. Johnson, Louisville, CO (US); Jason Case, Longmont, CO (US); Kari Riegner, Golden, CO (US); Robert H. Wham, Boulder, CO (US)

(73) Assignee: TYCO Healthcare Group LP, Mansfield, MA (US)

( * ) Notice: Subject to any disclaimer, the term of this patent is extended or adjusted under 35 U.S.C. 154(b) by 689 days.

This patent is subject to a terminal disclaimer.

(21) Appl. No.: 12/351,980

(22) Filed: Jan. 12, 2009

(65) Prior Publication Data
US 2010/0179536 A1    Jul. 15, 2010

(51) Int. Cl.
*A61B 18/18* (2006.01)
(52) U.S. Cl. .................. 606/38; 606/34; 606/32
(58) Field of Classification Search .......... 607/96, 607/98, 99; 606/32, 34, 38, 41
See application file for complete search history.

(56) References Cited

U.S. PATENT DOCUMENTS

| | | | |
|---|---|---|---|
| 4,200,104 A | 4/1980 | Harris | |
| 5,931,836 A | 8/1999 | Hatta | |
| 5,954,719 A | 9/1999 | Chen et al. | |
| 6,080,149 A | 6/2000 | Huang et al. | |
| 6,123,702 A | 9/2000 | Swanson et al. | |
| 6,183,468 B1 | 2/2001 | Swanson et al. | |
| 6,186,147 B1 | 2/2001 | Cobb | |
| 6,231,569 B1 | 5/2001 | Bek | |
| 6,245,065 B1 | 6/2001 | Panescu et al. | |
| 6,312,391 B1 | 11/2001 | Ramadhyani et al. | |
| 6,398,779 B1 | 6/2002 | Buysse et al. | |
| 6,423,057 B1 | 7/2002 | He et al. | |
| 6,494,880 B1 | 12/2002 | Swanson et al. | |
| 6,544,260 B1 | 4/2003 | Markel et al. | |

(Continued)

FOREIGN PATENT DOCUMENTS
DE    179607    3/1905
(Continued)

OTHER PUBLICATIONS
U.S. Appl. No. 12/057,557, filed Mar. 28, 2008.
(Continued)

*Primary Examiner* — Laura Bouchelle

(57) ABSTRACT

A method for controlling an electrosurgical waveform includes the initial steps of activating an electrosurgical generator and increasing power during a first sample window and determining a direction of change in a first average impedance during the first sample window. The method also includes the steps of performing a first adjustment of power in response to the direction of change in the first average impedance during a subsequent sample window and determining a direction of change in a subsequent average impedance during the subsequent sample window in response to the first adjustment of power. The method also includes performing a subsequent adjustment of power in response to the direction of change in the subsequent average impedance, wherein the subsequent adjustment of power is reverse to that of the first adjustment of power when the direction of change in the first and subsequent average impedances is the same.

15 Claims, 13 Drawing Sheets

U.S. PATENT DOCUMENTS

| | | |
|---|---|---|
| 6,936,047 B2 | 8/2005 | Nasab et al. |
| 6,939,346 B2 | 9/2005 | Kannenberg et al. |
| 6,962,587 B2 | 11/2005 | Johnson et al. |
| 7,226,447 B2 | 6/2007 | Uchida et al. |
| 7,258,688 B1 | 8/2007 | Shah et al. |
| 7,303,557 B2 | 12/2007 | Wham et al. |
| 2002/0068931 A1 | 6/2002 | Wong |
| 2003/0171745 A1 | 9/2003 | Francischelli |
| 2003/0199863 A1 | 10/2003 | Swanson et al. |
| 2004/0010289 A1 | 1/2004 | Biggs et al. |
| 2005/0004567 A1 | 1/2005 | Daniel |
| 2007/0173806 A1 | 7/2007 | Orszulak et al. |
| 2007/0282320 A1 | 12/2007 | Buysse et al. |
| 2007/0293858 A1 | 12/2007 | Fischer |
| 2008/0082095 A1 | 4/2008 | Shores |
| 2008/0262489 A1 | 10/2008 | Steinke |
| 2009/0234353 A1 | 9/2009 | McPherson |

FOREIGN PATENT DOCUMENTS

| | | |
|---|---|---|
| DE | 1099658 | 2/1961 |
| DE | 1139927 | 11/1962 |
| DE | 1149832 | 6/1963 |
| DE | 1439302 | 1/1969 |
| DE | 2439587 | 2/1975 |
| DE | 2455174 | 5/1975 |
| DE | 2407559 | 8/1975 |
| DE | 2602517 | 7/1976 |
| DE | 2504280 | 8/1976 |
| DE | 2540968 | 3/1977 |
| DE | 2820908 | 11/1978 |
| DE | 2803275 | 8/1979 |
| DE | 2823291 | 11/1979 |
| DE | 2946728 | 5/1981 |
| DE | 3143421 | 5/1982 |
| DE | 3045996 | 7/1982 |
| DE | 3120102 | 12/1982 |
| DE | 3510586 | 10/1986 |
| DE | 3604823 | 8/1987 |
| DE | 390937 | 4/1989 |
| DE | 3904558 | 8/1990 |
| DE | 3942998 | 7/1991 |
| DE | 4339049 | 5/1995 |
| DE | 19717411 | 11/1998 |
| DE | 19848540 | 5/2000 |
| EP | 246350 | 11/1987 |
| EP | 310431 | 4/1989 |
| EP | 325456 | 7/1989 |
| EP | 390937 | 10/1990 |
| EP | 556705 | 8/1993 |
| EP | 608609 | 8/1994 |
| EP | 836868 | 4/1998 |
| EP | 1051948 | 11/2000 |
| EP | 1472984 | 11/2004 |
| EP | 1500378 | 1/2005 |
| EP | 880220 | 6/2006 |
| EP | 1810630 | 7/2007 |
| EP | 1862137 | 12/2007 |
| FR | 1275415 | 10/1961 |
| FR | 1347865 | 11/1963 |
| FR | 2313708 | 12/1976 |
| FR | 2364461 | 7/1978 |
| FR | 2502935 | 10/1982 |
| FR | 2517953 | 6/1983 |
| FR | 2573301 | 5/1986 |
| GB | 607850 | 9/1948 |
| GB | 702510 | 1/1954 |
| GB | 855459 | 11/1960 |
| GB | 902775 | 8/1962 |
| GB | 2164473 | 3/1986 |
| GB | 2214430 | 9/1989 |
| GB | 2358934 | 8/2001 |
| SU | 166452 | 1/1965 |
| SU | 727201 | 4/1980 |
| WO | WO 9410922 | 5/1994 |
| WO | 01/74252 | 10/2001 |
| WO | 02/085229 | 10/2002 |
| WO | WO03047446 | 6/2003 |
| WO | 2004/083797 | 9/2004 |
| WO | 2008/002517 | 1/2008 |
| WO | WO2008003058 | 1/2008 |
| WO | WO2008011575 | 1/2008 |
| WO | WO 2008011575 A1 * | 1/2008 |
| WO | WO2008070562 | 6/2008 |
| WO | WO 2008070562 | 6/2008 |
| WO | 2009/075879 | 6/2009 |

OTHER PUBLICATIONS

U.S. Appl. No. 10/406,690, filed Apr. 3, 2003.
U.S. Appl. No. 11/242,458, filed Oct. 3, 2005.
U.S. Appl. No. 10/573,713, filed Mar. 28, 2006.
U.S. Appl. No. 12/136,620, filed Jun. 10, 2008.
U.S. Appl. No. 12/389,168, filed Feb. 19, 2009.
U.S. Appl. No. 12/351,935, filed Jan. 12, 2009.
U.S. Appl. No. 12/401,981, filed Mar. 11, 2009.
U.S. Appl. No. 12/351,947, filed Jan. 12, 2009.
U.S. Appl. No. 12/407,896, filed Mar. 20, 2009.
U.S. Appl. No. 12/205,525, filed Sep. 5, 2008.
U.S. Appl. No. 12/249,263, filed Oct. 10, 2008.
U.S. Appl. No. 12/249,218, filed Oct. 10, 2008.
U.S. Appl. No. 12/351,970, filed Jan. 12, 2009.
U.S. Appl. No. 12/351,960, filed Jan. 12, 2009.
U.S. Appl. No. 12/205,298, filed Sep. 5, 2008.
U.S. Appl. No. 12/351,980, filed Jan. 12, 2009.
U.S. Appl. No. 12/203,734, filed Sep. 3, 2008.
U.S. Appl. No. 12/242,102, filed Sep. 30, 2008.
U.S. Appl. No. 12/241,861, filed Sep. 30, 2008.
U.S. Appl. No. 12/242,061, filed Sep. 30, 2008.
U.S. Appl. No. 12/242,026, filed Sep. 30, 2008.
U.S. Appl. No. 12/241,905, filed Sep. 30, 2008.
U.S. Appl. No. 12/241,942, filed Sep. 30, 2008.
U.S. Appl. No. 12/241,983, filed Sep. 30, 2008.
Wald et al., "Accidental Burns", JAMA, Aug. 16, 1971, vol. 217, No. 7, pp. 916-921.
Vallfors et al., "Automatically Controlled Bipolar Electrosoagulation-'COA-COMP'" Neurosurgical Review 7:2-3 (1984) pp. 187-190.
Sugita et al., "Bipolar Coagulator with Automatic Thermocontrol" J. Neurosurg., vol. 41, Dec. 1944, pp. 777-779.
Muller et al. "Extended Left Hemicolectomy Using the LigaSure Vessel Sealing System" Innovations That Work; Company Newsletter; Sep. 1999.
Ogden Goertzel Alternative to the Fourier Transform: Jun. 1993 pp. 485-487 Electronics World; Reed Business Publishing, Sutton, Surrey, BG vol. 99, No. 9. 1687.
Hadley I C D et al., "Inexpensive Digital Thermometer for Measurements on Semiconductors" International Journal of Electronics; Taylor and Francis. Ltd.; London, GB; vol. 70, No. 6 Jun. 1, 1991; pp. 1155-1162.
Richard Wolf Medical Instruments Corp. Brochure, "Kleppinger Bipolar Forceps & Bipolar Generator" 3 pp. Jan. 1989.
Astrahan, "A Localized Current Field Hyperthermia System for Use with 192-Iridium Interstitial Implants" Medical Physics, 9 (3), May/Jun. 1982.
Alexander et al., "Magnetic Resonance Image-Directed Stereotactic Neurosurgery: Use of Image Fusion with Computerized Tomography to Enhance Spatial Accuracy" Journal Neurosurgery, 83; (1995) pp. 271-276.
Geddes et al., "The Measurement of Physiologic Events by Electrical Impedance" Am. J. MI, Jan. Mar. 1964, pp. 16-27.
Cosman et al., "Methods of Making Nervous System Lesions" In William RH, Rengachary SS (eds): Neurosurgery, New York: McGraw-Hill, vol. 111, (1984), pp. 2490-2499.
Anderson et al., "A Numerical Study of Rapid Heating for High Temperature Radio Frequency Hyperthermia" International Journal of Bio-Medical Computing, 35 (1994) pp. 297-307.
Cosman et al., "Radiofrequency Lesion Generation and Its Effect on Tissue Impedance" Applied Neurophysiology 51: (1988) pp. 230-242.

Ni W. et al. "A Signal Processing Method for the Coriolis Mass Flowmeter Based on a Normalized . . ." Journal of Applied Sciences-Yingyong Kexue Xuebao, Shangha CN, vol. 23 No. 2;(Mar. 2005); pp. 160-164.
Chicharo et al. "A Sliding Goertzel Algorith" Aug. 1996, pp. 283-297 Signal Processing, Elsevier Science Publishers B.V. Amsterdam, NL vol. 52 No. 3.
Bergdahl et al., "Studies on Coagulation and the Development of an Automatic Computerized Bipolar Coagulator" Journal of Neurosurgery 75:1, (Jul. 1991) pp. 148-151.
Cosman et al., "Theoretical Aspects of Radiofrequency Lesions in the Dorsal Root Entry Zone" Neurosurgery 15:(1984) pp. 945-950.
Goldberg et al., "Tissue Ablation with Radiofrequency: Effect of Probe Size, Gauge, Duration, and Temperature on Lesion Volume" Acad Radio (1995) vol. 2, No. 5, pp. 399-404.
Medtrex Brochure—Total Control at Full Speed, "The O.R. Pro 300" 1 p. Sep. 1998.
Valleylab Brochure "Valleylab Electroshield Monitoring System" 2 pp. Nov. 1995.
International Search Report EP 98300964.8 dated Dec. 4, 2000.
International Search Report EP 04009964 dated Jul. 13, 2004.
International Search Report EP 04015981.6 dated Sep. 29, 2004.
International Search Report EP04707738 dated Jul. 4, 2007.
International Search Report EP 05002769.7 dated Jun. 9, 2006.
International Search Report EP 05014156.3 dated Dec. 28, 2005.
International Search Report EP 05021944.3 dated Jan. 18, 2006.
International Search Report EP 05022350.2 dated Jan. 18, 2006.
International Search Report EP 06000708.5 dated Apr. 21, 2006.
International Search Report—extended EP 06000708.5 dated Aug. 22, 2006.
International Search Report EP 06006717.0 dated Aug. 7, 2006.
International Search Report EP 06010499.9 dated Jan. 29, 2008.
International Search Report EP 06022028.2 dated Feb. 5, 2007.
International Search Report EP 06025700.3 dated Apr. 12, 2007.
International Search Report EP 07001481.6 dated Apr. 23, 2007.
International Search Report EP 07001485.7 dated May 15, 2007.
International Search Report EP 07001489.9 dated Dec. 20, 2007.
International Search Report EP 07001491 dated Jun. 6, 2007.
International Search Report EP 07001527.6 dated May 9, 2007.
International Search Report EP 07004355.9 dated May 21, 2007.
International Search Report EP 07008207.8 dated Sep. 13, 2007.
International Search Report EP 07009322.4 dated Jan. 14, 2008.
International Search Report EP 07010673.7 dated Sep. 24, 2007.
International Search Report EP 07015601.3 dated Jan. 4, 2008.
International Search Report EP 07015602.1 dated Dec. 20, 2007.
International Search Report EP 07019174.7 dated Jan. 29, 2008.
International Search Report EP08004667.5 dated Jun. 3, 2008.
International Search Report EP08006733.3 dated Jul. 28, 2008.
International Search Report EP08012503 dated Sep. 19, 2008.
International Search Report EP08013605 dated Nov. 17, 2008.
International Search Report EP08015601.1 dated Dec. 5, 2008.
International Search Report EP08155780 dated Jan. 19, 2009.
International Search Report EP08016540.0 dated Feb. 25, 2009.
International Search Report EP08166208.2 dated Dec. 1, 2008.
International Search Report PCT/US03/33711 dated Jul. 16, 2004.
International Search Report PCT/US03/33832 dated Jun. 17, 2004.
International Search Report PCT/US03/37110 dated Jul. 25, 2005.
International Search Report PCT/US03/37310 dated Aug. 13, 2004.
International Search Report PCT/US04/02961 dated Aug. 2, 2005.
International Search Report EP 10164740 dated Aug. 3, 2010.
European Search Report, Application No. EP 10 00 9732 dated Jan. 18, 2011.
International Search Report EP 10150566 dated Jun. 10, 2010.
International Search Report EP 10150567 dated Jun. 10, 2010.
International Search Report EP 10150563 dated Jun. 10, 2010.

* cited by examiner

ENERGY DELIVERY ALGORITHM FOR MEDICAL DEVICES BASED ON MAINTAINING A FIXED POSITION ON A TISSUE ELECTRICAL CONDUCTIVITY V. TEMPERATURE CURVE

BACKGROUND

1. Technical Field

The present disclosure relates to electrosurgical apparatuses, systems and methods. More particularly, the present disclosure is directed to an algorithm that controls the application of energy to tissue.

2. Background of Related Art

Electrosurgical generators are employed by surgeons in conjunction with an electrosurgical instrument to cut, coagulate, desiccate and/or seal patient tissue. High frequency electrical energy, e.g., radio frequency (RF) energy, is produced by the electrosurgical generator and applied to the tissue by the electrosurgical tool. Both monopolar and bipolar configurations are commonly used during electrosurgical procedures.

Electrosurgical techniques and instruments can be used to coagulate small diameter blood vessels or to seal large diameter vessels or tissue, e.g., soft tissue structures, such as lung, brain and intestine. A surgeon can either cauterize, coagulate/desiccate and/or simply reduce or slow bleeding, by controlling the intensity, frequency and duration of the electrosurgical energy applied between the electrodes and through the tissue. In order to achieve one of these desired surgical effects without causing unwanted charring of tissue at the surgical site or causing collateral damage to adjacent tissue, e.g., thermal spread, it is necessary to control the output from the electrosurgical generator, e.g., power, waveform voltage, current, pulse rate, etc.

It is known that measuring the electrical impedance and change thereof across the tissue at the surgical site provides a good indication of the state of desiccation or drying of the tissue, e.g., as the tissue dries or loses moisture, the impedance across the tissue rises. This observation has been utilized in some electrosurgical generators to regulate the electrosurgical power based on a measurement of tissue impedance. For example, commonly-owned U.S. Pat. No. 6,210,403 relates to a system and method for automatically measuring the tissue impedance and altering the output of the electrosurgical generator based on the measured impedance across the tissue.

It has been determined that the particular waveform of electrosurgical energy can be tailored to enhance a desired surgical effect, e.g., cutting, coagulation, sealing, blend, etc. For example, the "cutting" mode typically entails generating an uninterrupted sinusoidal waveform in the frequency range of 100 kHz to 4 MHz with a crest factor in the range of 1.4 to 2.0. The "blend" mode typically entails generating an uninterrupted cut waveform with a duty cycle in the range of 25% to 75% and a crest factor in the range of 2.0 to 5.0. The "coagulate" mode typically entails generating an uninterrupted waveform with a duty cycle of approximately 10% or less and a crest factor in the range of 5.0 to 12.0. In order to effectively and consistently seal vessels or tissue, a pulse-like waveform is preferred. Energy may be supplied in a continuous fashion to seal vessels in tissue if the energy input/output is responsive to tissue hydration/volume through feedback control. Delivery of the electrosurgical energy in pulses allows the tissue to cool down and also allows some moisture to return to the tissue between pulses which are both known to enhance the sealing process.

SUMMARY

The present disclosure relates to a method for controlling an electrosurgical waveform generated by an electrosurgical generator. The method includes the initial steps of activating an electrosurgical generator to produce an electrosurgical waveform and increasing power of the electrosurgical waveform during a first sample window. The method also includes the steps of determining a direction of change in a first average impedance during the first sample window in response to the increase in power of the electrosurgical waveform and performing a first adjustment of power of the electrosurgical waveform in response to the direction of change in the first average impedance during a subsequent sample window. The method also includes the steps of determining a direction of change in a subsequent average impedance during the subsequent sample window in response to the first adjustment of power and performing a subsequent adjustment of power of the electrosurgical waveform in response to the direction of change in the subsequent average impedance, wherein the subsequent adjustment of power is reverse (i.e., adjusted in the opposite direction) to that of the first adjustment of power when the direction of change in the first and subsequent average impedances is the same.

According to another embodiment of the present disclosure, a method for controlling an electrosurgical waveform generated by an electrosurgical generator includes the initial steps of activating an electrosurgical generator to produce an electrosurgical waveform and increasing power of the electrosurgical waveform during a first sample window of a normal priority task. The method also includes the steps of determining a direction of change in a first average impedance during the first sample window of the normal priority task in response to the increase in power of the electrosurgical waveform and performing a first adjustment of power of the electrosurgical waveform in response to the direction of change in the first average impedance during a subsequent sample window of the normal priority task. The method also includes the steps of determining a direction of change in a subsequent average impedance during the subsequent sample window of the normal priority task in response to the first adjustment of power and performing a subsequent adjustment of power of the electrosurgical waveform in response to the direction of change in the subsequent average impedance, wherein the subsequent adjustment of power is reverse (i.e., adjusted in the opposite direction) to that of the first adjustment of power when the direction of change in the first and subsequent average impedances is the same.

According to another embodiment of the present disclosure, a control system for use with an electrosurgical generator adapted to generate an electrosurgical waveform for application to tissue includes a controller configured to adjust power of an electrosurgical waveform generated by an electrosurgical generator. The controller increases power of the electrosurgical waveform during a first sample window. A sensor module is configured to continually sense tissue impedance resulting from the application of the electrosurgical waveform to the tissue and generate at least one signal relating to the application of the electrosurgical waveform to the tissue. At least one loop control module is in operative communication with the controller for receiving the at least one signal from the sensor module to determine a direction of change in a first average impedance during the first sample window in response to the increase in power of the electrosurgical waveform made by the controller. The controller performs a first adjustment of power of the electrosurgical waveform in response to the direction of change in the first average impedance during a subsequent sample window. The at least one loop control module is further configured to determine a direction of change in a subsequent average impedance during the subsequent sample window in response to the first adjustment of power made by the controller. The controller is further configured to perform a subsequent adjustment of power of the electrosurgical waveform in response to the direction of change in the subsequent average impedance, wherein the subsequent adjustment of power is reverse (i.e., adjusted in the opposite direction) to that of the first adjustment of power when the direction of change in the first and subsequent average impedances is the same.

BRIEF DESCRIPTION OF THE DRAWINGS

Various embodiments of the present disclosure are described herein with reference to the drawings wherein.

DETAILED DESCRIPTION

Particular embodiments of the present disclosure will be described hereinbelow with reference to the accompanying drawings. In the following description, well-known functions or constructions are not described in detail to avoid obscuring the present disclosure in unnecessary detail. Those skilled in the art will understand that the present disclosure may be adapted for use with either an endoscopic instrument or an open instrument.

A generator according to the present disclosure can perform monopolar and bipolar electrosurgical procedures, including tissue ablation procedures. The generator may include a plurality of outputs for interfacing with various electrosurgical instruments (e.g., a monopolar active electrode, return electrode, bipolar electrosurgical forceps, footswitch, etc.). Further, the generator includes electronic circuitry configured for generating radio frequency power specifically suited for various electrosurgical modes (e.g., cutting, blending, division, etc.) and procedures (e.g., monopolar, bipolar, vessel scaling).

Figure 1:
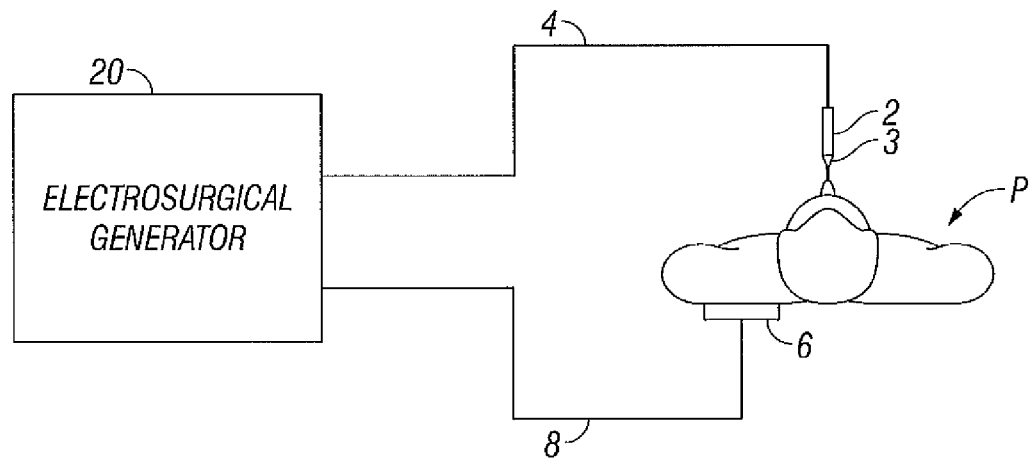
FIG. 1A is a schematic block diagram of a monopolar electrosurgical system according to the present disclosure.
FIG. 1B is a schematic block diagram of a bipolar electrosurgical system according to the present disclosure.

FIG. 1 is a schematic illustration of a monopolar electrosurgical system according to one embodiment of the present disclosure. The system includes a monopolar electrosurgical instrument 2 including one or more active electrodes 3, which can be electrosurgical cutting probes, ablation electrode(s), etc. Electrosurgical RF energy is supplied to the instrument 2 by a generator 20 via a supply line 4, which is connected to an active terminal 30 (FIG. 2) of the generator 20, allowing the instrument 2 to coagulate, ablate and/or otherwise treat tissue. The energy is returned to the generator 20 through a return electrode 6 via a return line 8 at a return terminal 32 (FIG. 2) of the generator 20. The active terminal 30 and the return terminal 32 are connectors configured to interface with plugs (not explicitly shown) of the instrument 2 and the return electrode 6, which are disposed at the ends of the supply line 4 and the return line 8, respectively.

The system may include a plurality of return electrodes 6 that are arranged to minimize the chances of tissue damage by maximizing the overall contact area with the patient P. In addition, the generator 20 and the return electrode 6 may be configured for monitoring so-called "tissue-to-patient" contact to insure that sufficient contact exists therebetween to further minimize chances of tissue damage.

Not explicitly shown in FIG. 1, the generator 20 includes suitable input controls (e.g., buttons, activators, switches, touch screen, etc.) for controlling the generator 20, as well as one or more display screens for providing the surgeon with variety of output information (e.g., intensity settings, treatment complete indicators, etc.). The controls allow the surgeon to adjust power of the RF energy, waveform, and other parameters to achieve the desired waveform suitable for a particular task (e.g., tissue ablation). Further, the instrument 2 may include a plurality of input controls which may be redundant with certain input controls of the generator 20. Placing the input controls at the instrument 2 allows for easier and faster modification of RF energy parameters during the surgical procedure without requiring interaction with the generator 20.

Figure 2:
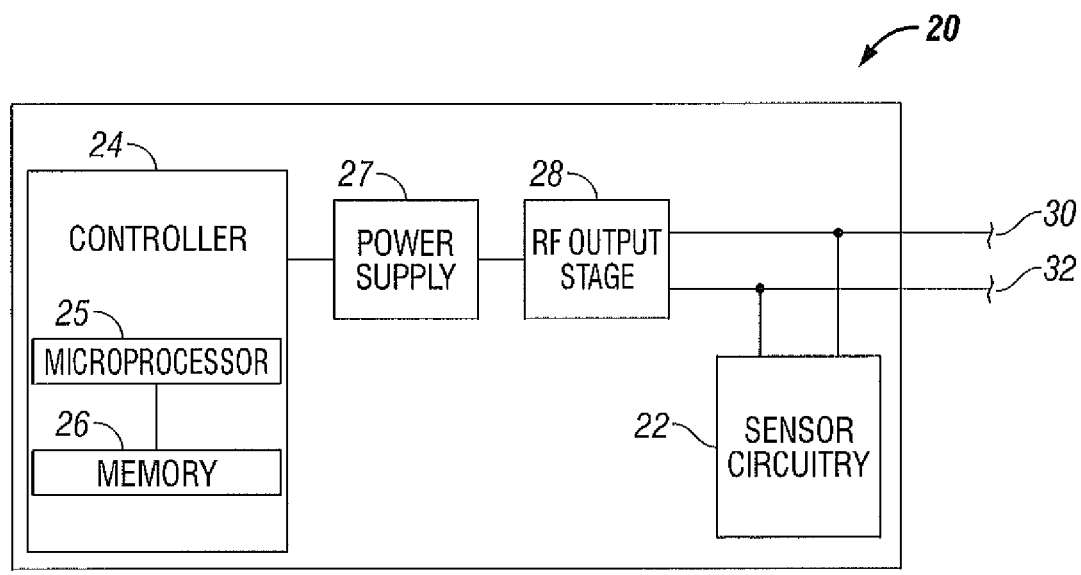
FIG. 2 is a schematic block diagram of a generator control system according to one embodiment of the present disclosure.

FIG. 2 shows a schematic block diagram of the generator 20 having a controller 24, a power supply 27, an RF output stage 28, and a sensor module 22. The power supply 27 may provide DC power to the RF output stage 28 which then converts the DC power into RF energy and delivers the RF energy to the instrument 2. The controller 24 includes a microprocessor 25 having a memory 26 which may be volatile type memory (e.g., RAM) and/or non-volatile type memory (e.g., flash media, disk media, etc.). The microprocessor 25 includes an output port connected to the power supply 27 and/or RF output stage 28 which allows the microprocessor 25 to control the output of the generator 20 according to either open and/or closed control loop schemes.

A closed loop control scheme generally includes a feedback control loop wherein the sensor module 22 provides feedback to the controller 24 (i.e., information obtained from one or more sensing mechanisms for sensing various tissue parameters such as tissue impedance, tissue temperature, output current and/or voltage, etc.). The controller 24 then signals the power supply 27 and/or RF output stage 28 which then adjusts the DC and/or RF power supply, respectively. The controller 24 also receives input signals from the input controls of the generator 20 and/or instrument 2. The controller 24 utilizes the input signals to adjust the power output of the generator 20 and/or instructs the generator 20 to perform other control functions.

The microprocessor 25 is capable of executing software instructions for processing data received by the sensor module 22, and for outputting control signals to the generator 20, accordingly. The software instructions, which are executable by the controller 24, are stored in the memory 26 of the controller 24.

The controller 24 may include analog and/or logic circuitry for processing the sensed values and determining the control signals that are sent to the generator 20, rather than, or in combination with, the microprocessor 25.

The sensor module 22 may include a plurality of sensors (not explicitly shown) strategically located for sensing various properties or conditions, e.g., tissue impedance, voltage at the tissue site, current at the tissue site, etc. The sensors are provided with leads (or wireless) for transmitting information to the controller 24. The sensor module 22 may include control circuitry which receives information from multiple sensors, and provides the information and the source of the information (e.g., the particular sensor providing the information) to the controller 24.

More particularly, the sensor module 22 may include a real-time voltage sensing system (not explicitly shown) and a real-time current sensing system (not explicitly shown) for sensing real-time values related to applied voltage and current at the surgical site. Additionally, an RMS voltage sensing system (not explicitly shown) and an RMS current sensing system (not explicitly shown) may be included for sensing and deriving RMS values for applied voltage and current at the surgical site.

The measured or sensed values are further processed, either by circuitry and/or a processor (not explicitly shown) in the sensor module 22 and/or by the controller 24, to determine changes in sensed values and tissue impedance. Tissue impedance and changes therein may be determined by measuring the voltage and/or current across the tissue and then calculating changes thereof over time. The measured and calculated values may be then compared with known or desired voltage and current values associated with various tissue types, procedures, instruments, etc. This may be used to drive electrosurgical output to achieve desired impedance and/or change in impedance values. As the surgical procedure proceeds, tissue impedance fluctuates in response to adjustments in generator output as well as removal and restoration of liquids (e.g., steam bubbles) from the tissue at the surgical site. The controller 24 monitors the tissue impedance and changes in tissue impedance and regulates the output of the generator 20 in response thereto to achieve the desired and optimal electrosurgical effect.

In general, the system according to the present disclosure regulates the application of energy to achieve the desired tissue treatment based on properties (e.g., electrical and/or physical) of tissue. In embodiments, the application of energy to tissue is regulated based on the electrical conductivity of that tissue as a function of the tissue temperature. Tissue conductivity as a function of tissue temperature may be represented as a conductivity vs. temperature curve. Tissue conductance is inversely related to tissue impedance if the material tissue properties (e.g., length of tissue, area of tissue, etc.) remain constant. Specifically, tissue conductance and tissue impedance are related by the following equation:

$$Z = L/(\sigma * A);$$

where Z is impedance of tissue undergoing treatment;
L is the length of tissue undergoing treatment;
σ is electrical conductance of tissue undergoing treatment; and
A is the surface area of tissue undergoing treatment.

Figure 3:
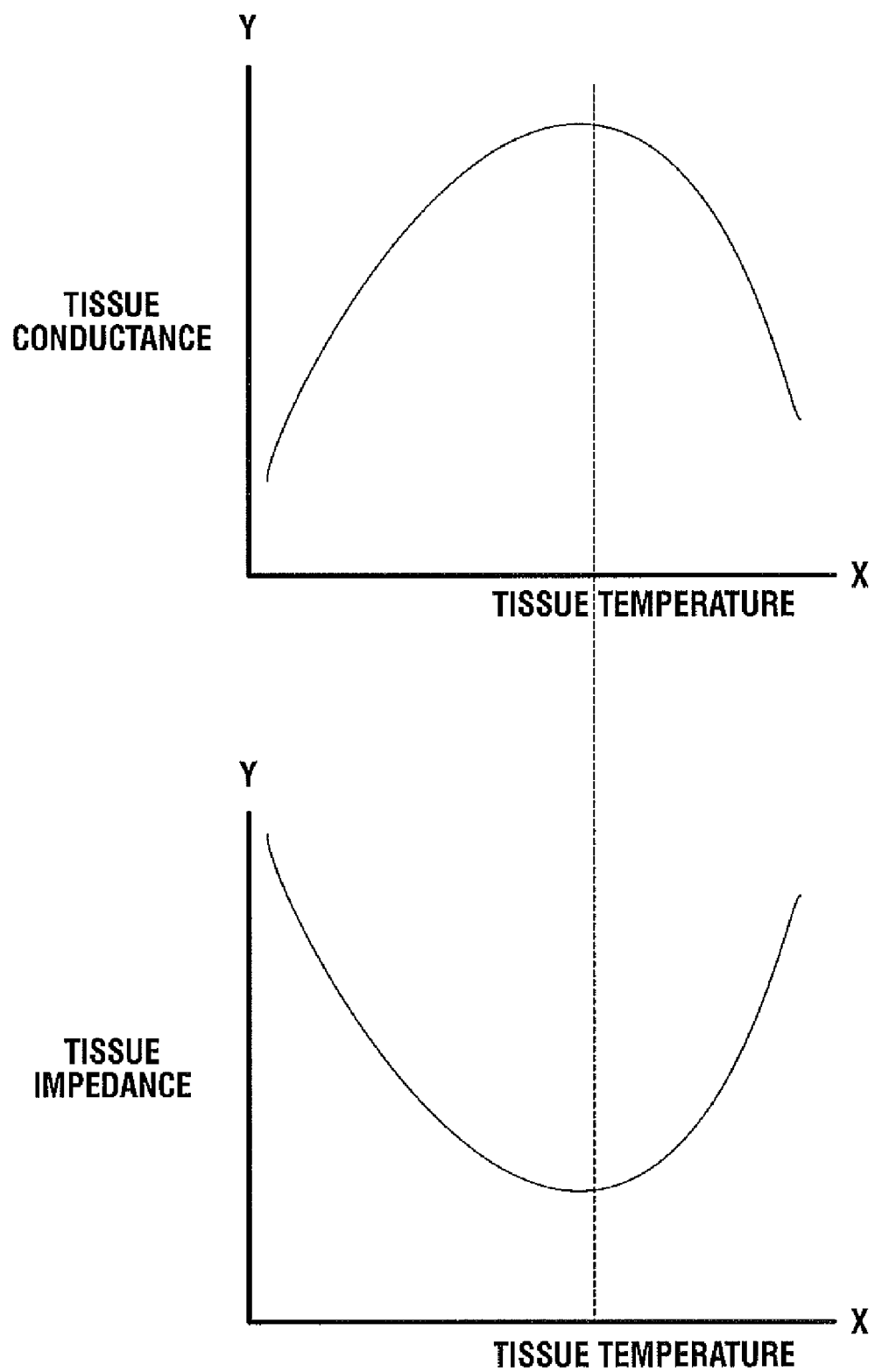
FIG. 3 illustrates a relationship between a tissue conductivity vs. temperature curve and a tissue impedance vs. temperature curve for tissue undergoing treatment.

FIG. 3 illustrates the relationship between a typical conductivity vs. temperature curve and a corresponding (i.e., over the same temperature range) impedance vs. temperature curve for tissue undergoing ablation (e.g., utilizing electrosurgical instrument 2). The illustrated curves demonstrate that, for tissue undergoing ablation, the lowest impedance value on the impedance vs. temperature curve corresponds to the highest conductance value on the conductance vs. temperature curve.

The conductance vs. temperature curve for tissue undergoing ablation may be dynamically changing due a variety of factors such as, for example, the changes in energy applied to tissue. The present disclosure provides for a control algorithm that actively tracks this curve to allow for the application of energy to maintain an optimal positioning on the curve (e.g., peak tissue conductance) despite the dynamic nature of the curve.

FIG. 4 shows a flow chart illustrating a control algorithm 200 for regulating the application of energy to tissue, according to one embodiment of the present disclosure. In embodiments, algorithm 200 may be a software application residing in the memory 26 and executable by the controller 24 (e.g., via the microprocessor 25).

The control algorithm defines a state variable (SV) to express a real-time value of one or more physical properties of the tissue undergoing ablation (e.g., tissue impedance, voltage across tissue, current through tissue) and/or one or more electrical properties related to the applied energy (e.g., amplitude and/or phase of power applied to tissue, etc.). In embodiments, the SV may be defined in any one or more so-called "states". For example, the SV may represent the real-time state of tissue resistance as being either "decreasing" or "rising".

Figure 4A:
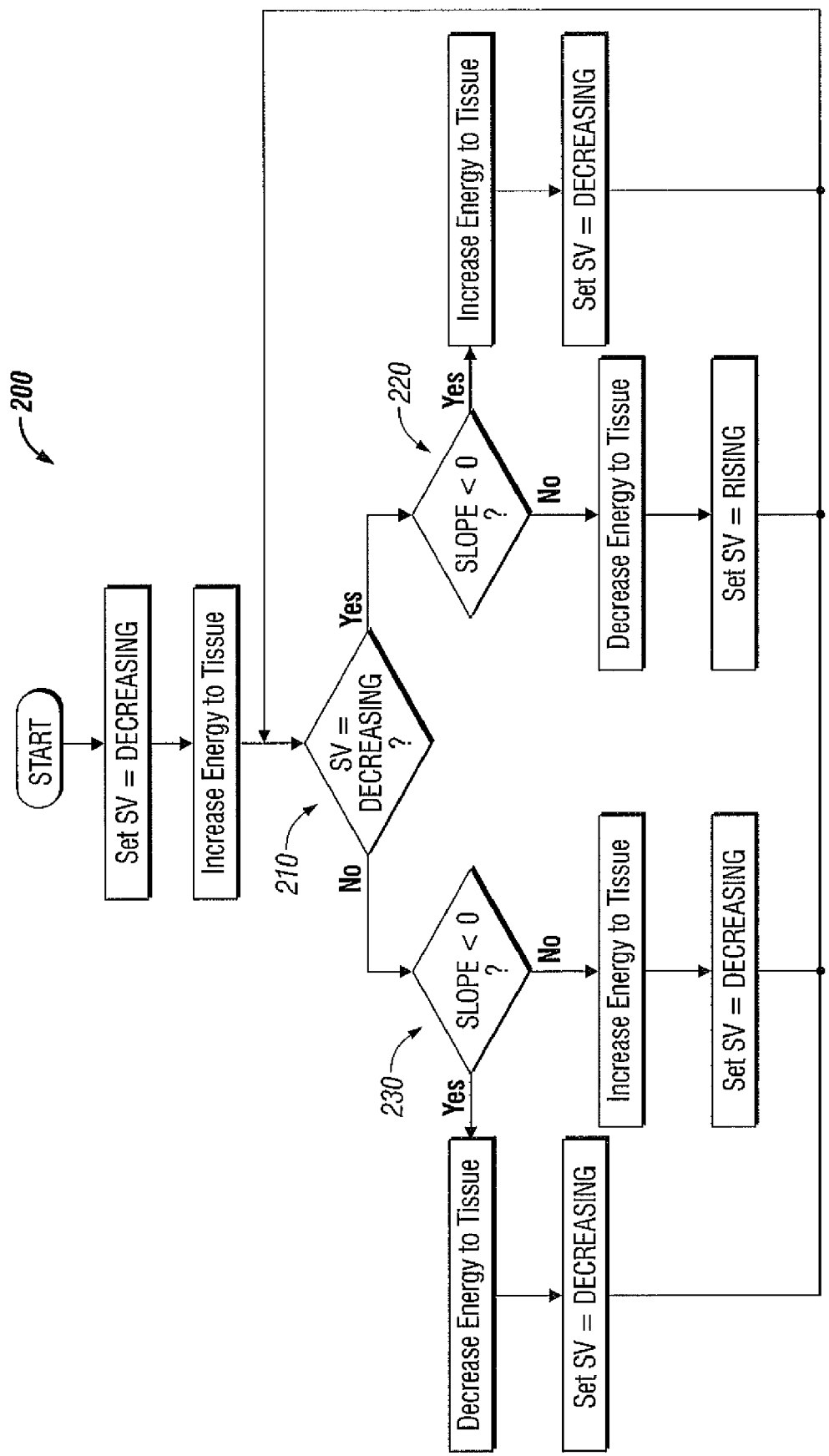
FIG. 4A is a schematic block diagram of a control algorithm according to embodiments of the present disclosure.

In the embodiment illustrated in FIG. 4A, the algorithm 200 initially defines the SV as decreasing and increases the application of energy to tissue (e.g., the controller 24 increases the output of the generator 20). Subsequently, the control algorithm 200 enters a switch loop 210 wherein the algorithm 200 continuously monitors the SV to be in any one of two states (e.g., decreasing or rising). Based on the detected state of the SV, the algorithm 200 switches between two control loops to control the application of energy to tissue.

In the illustrated embodiment, the algorithm 200 enters one of two control loops 220 and 230 to correspond to decreasing and rising states of the SV, respectively, as detected by the algorithm 200 via the switch loop 210. More specifically, the algorithm 200 enters a decreasing case control loop 220 if the switch loop 210 detects the state of the SV as decreasing. Upon entering control loop 220, the algorithm 200 continuously detects (e.g., via the sensor module 22) the slope of the control curve (e.g., the impedance vs. temperature curve of FIG. 3). If the detected slope of the control curve is negative, the algorithm 200 increases the application of energy to tissue (e.g., the controller 24 increases the output of the generator 20) and subsequently defines the SV as decreasing. In this manner, the decreasing case control loop 220 is repeated as long as the SV is defined as decreasing and the slope of the control curve is negative.

Conversely, if the detected slope of the control curve is not negative (e.g., slope=0 or slope>0), the algorithm 200 decreases the application of energy to tissue and subsequently defines the SV as rising. In this manner, the switch loop 210 detects the SV as rising and, thus, triggers the algorithm 200 to enter a rising case control loop 230.

Upon entering the rising case control loop 230, the algorithm 200 continuously detects the slope of the control curve. The rising case control loop 230 is configured such that the response to the detected slope of the control curve is directly opposite to that of the decreasing case control loop 220. More specifically, if the detected slope of the control curve is negative during the rising case control loop 230, the algorithm 200 continues to decrease the application of energy to tissue (e.g., the controller 24 further decreases the output of the generator 20) and subsequently defines the SV as decreasing. Continuing to decrease the application of energy to tissue in this scenario allows the algorithm 200 to effectively track the optimal point on the control curve (e.g., lowest possible tissue impedance as a function of temperature). Conversely, if the detected slope of the control curve is not negative (e.g., slope=0 or slope>0), the algorithm 200 increases the application of energy to tissue and subsequently defines the SV as decreasing. Increasing the application of energy to tissue in this scenario allows the algorithm 200 to effectively deliver the maximum energy to tissue. In either scenario (i.e., slope<0; and slope>0) of the rising case control loop 230, the SV is reset to decreasing such that the algorithm 200 enters or re-enters the decreasing case control loop 220. In this way, the algorithm 200 aggressively applies energy to tissue to achieve maximal tissue heating while tracking the optimal point on the control curve (e.g., the lowest possible tissue impedance).

In embodiments wherein a tissue impedance vs. temperature curve (e.g., FIG. 3) is utilized as the control curve, the decreasing case control loop 220 recognizes that a slope detected as negative corresponds to the tissue impedance as decreasing and, thus, the algorithm 200 increases the application of energy to tissue accordingly and re-enters the decreasing case control loop 220. Conversely, the decreasing case control loop 220 recognizes that a slope detected as not negative corresponds to the tissue impedance as rising and, thus, the algorithm 200 decreases the application of energy to tissue accordingly and enters the rising case control loop 230. The rising case control loop 230 recognizes that a slope detected as negative corresponds to the tissue impedance as decreasing and, thus, the algorithm 200 further decreases the application of energy to tissue to ensure the algorithm 200 finds the lowest possible tissue impedance. Conversely, the rising case control loop 230 recognizes that a slope detected as not negative corresponds to the tissue impedance as not changing or continuing to rise and, thus, the algorithm 200 increases the application of energy to tissue to ensure that the maximum energy is delivered to tissue.

Figure 4B:
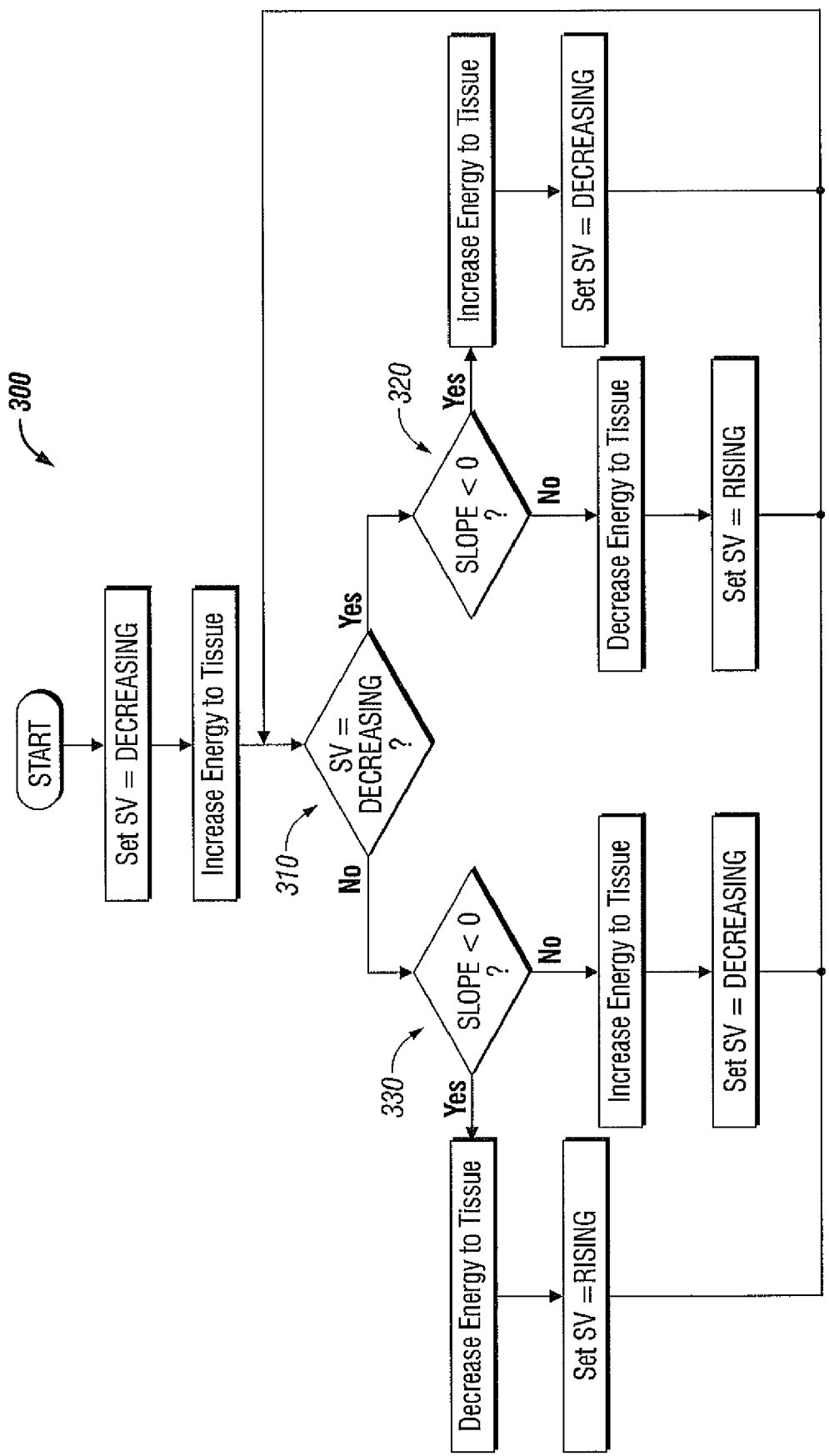
FIG. 4B is a schematic block diagram of a control algorithm according to an embodiment of the present disclosure.

In embodiments, in the case of the SV being defined as rising, if the slope of the control curve is negative, energy applied to tissue is decreased and the SV is reset to rising rather than decreasing, as is the case in the embodiment illustrated in FIG. 4A. FIG. 4B shows a flow chart illustrating an alternative algorithm 300 according to embodiments of the present disclosure. The algorithm 300 operates similarly to the algorithm 200 illustrated in FIG. 4A and is only described to the extent necessary to illustrate the differences between the embodiments. The algorithm 300 utilizes the identical initialization as that of the algorithm 200 illustrated in FIG. 4A. Further, the algorithm 300 includes a switch loop 310 configured to switch between two control loops, namely, a decreasing case control loop 320 and a rising case control loop 330 corresponding to the SV being defined as decreasing and rising, respectively.

As illustrated in FIGS. 4A and 4B, the difference between the algorithms 200 and 300 lies in the respective rising case control loops 230 and 330. In the case of the SV being defined as rising in the switch loop 310 of the algorithm 300, if the slope of the control curve is negative, the algorithm 300 decreases the energy applied to tissue and maintains the SV as rising rather than reset to decreasing, as is the case in the algorithm 200 embodied in FIG. 4A. In this manner, the rising case control loop 330 will continue to loop until the slope of the control curve is not negative (e.g., slope=0 or slope>0). In embodiments wherein a tissue impedance vs. temperature curve (e.g., FIG. 3) is utilized as the control curve, if the tissue impedance is decreasing (e.g., slope of the control curve<0), the rising case control loop 330 will continue until the algorithm 300 detects that the tissue impedance is not negative (i.e., slope of the control curve>0). Upon detection that the tissue impedance is not negative, the algorithm 300 increases the application of energy to tissue and resets the SV to decreasing.

In embodiments, a high priority control loop may be layered over the algorithms 200 and 300 to run concurrently therewith. During the ablation of tissue, conditions may exist that lead to continued energy increases. Such energy increases may cause tissue properties (e.g., impedance) to rise and/or fall outside of the peak conductance range or into a so-called "runaway state." The high priority control loop monitors the control curve for the runaway state and adjusts the application of energy (e.g., the controller 24 decreases the output of the generator 20) accordingly. More specifically, the high priority loop interrupts the algorithm (e.g., algorithm 200 and 300) to check for the runaway state, and decreases the application of energy in the event that such a state is detected. In embodiments wherein an impedance vs. temperature curve (FIG. 3) is utilized as the control curve, the high priority loop continually interrogates whether tissue impedance is rising more than a pre-determined threshold value. The predetermined threshold value may be pre-determined by the surgeon via the generator 20 input controls and/or reside in the memory 26 for execution by the microprocessor 25.

Figure 5:
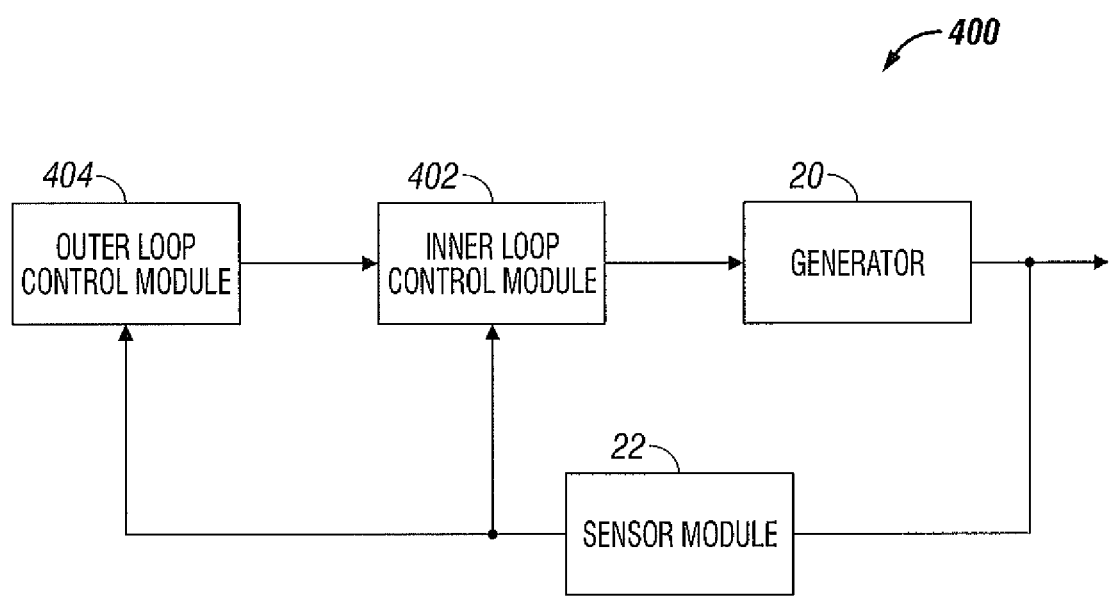
FIG. 5 is a schematic block diagram of a dual loop control system for use with the generator of FIG. 2.

With reference to FIG. 5, another embodiment of the present disclosure is shown. In the illustrated embodiment, energy application is regulated by the controller 24 pursuant to a closed loop control system 400 stored within the memory 26. The system 400 continuously monitors tissue impedance as an indicator of tissue conductance and automatically adjusts output to create the lowest possible tissue impedance and/or the highest possible tissue conductance. Upon the initialization of a given procedure or at some predetermined time delay thereafter, the system 400 processes and stores a baseline impedance $Z_{BASE}$ determined by the sensor 24. The system 400 determines deviations in average tissue impedance from the baseline impedance $Z_{BASE}$ as a function of time and adjusts generator 20 output in response to such deviations. This allows peak tissue conductance to be maintained independent of tissue changes, variations in generator 20 output, and device accessory selection.

Further, the system 400 continually interrogates whether detected impedance has risen above a threshold value, and reduces generator output in response to any such threshold breaches. Finally, the system 400 may commence a treatment termination sequence upon detection of specific tissue conditions which indicate a completed treatment. Treatment completion may be indicated by an equilibrium between the level of energy applied to the tissue (e.g., via the forceps 10)

and the level of energy dissipated from the tissue. Based on this equilibrium, the system 400 determines that the detected tissue impedance has achieved its lowest sustainable level and has remained at that level without change for a substantial amount of time.

Accordingly, the closed loop control system 400 of the present disclosure provides continual control of the power supply 27 and/or the output stage 28 (FIG. 2) in response to so-called "sensed" physical or electrical properties at the surgical site and/or proximate the output stage 28. In embodiments of the present disclosure and in particular reference to FIG. 5, the controller 24 may be provided with and/or in operative communication with an inner loop control module 402 and an outer loop control module 404 through which various priority tasks (e.g., loops) may be executed. The inner and outer loop control modules 402, 404 may be software modules executable by the microprocessor 25 of the controller 24 (FIG. 2) and both may receive signals generated by the sensor module 22.

The inner and outer loop control modules 402, 404 continually receive real-time sensed values, such as current I and voltage V, from the sensor module 22 as well as a time t. The modules 402, 404 perform calculations on the sensed values to derive additional real-time values, such as power P and impedance Z. For example, the value for change in impedance (dz/dt) is obtained in accordance with:

$$dz/dt = (Z - Z\_OLD)/(t - t\_OLD); \text{ and}$$

$$Z\_OLD = Z;$$

where Z is the impedance in accordance with values measured at time t; and

Z_OLD is the stored impedance in accordance with values measured at a previous time interval at time t_OLD. The inner and outer loop control modules 402, 404 process the real-time sensed values and output an RF command to the generator 20 which controls the output power needed for achieving a desired tissue effect.

Figure 6A:
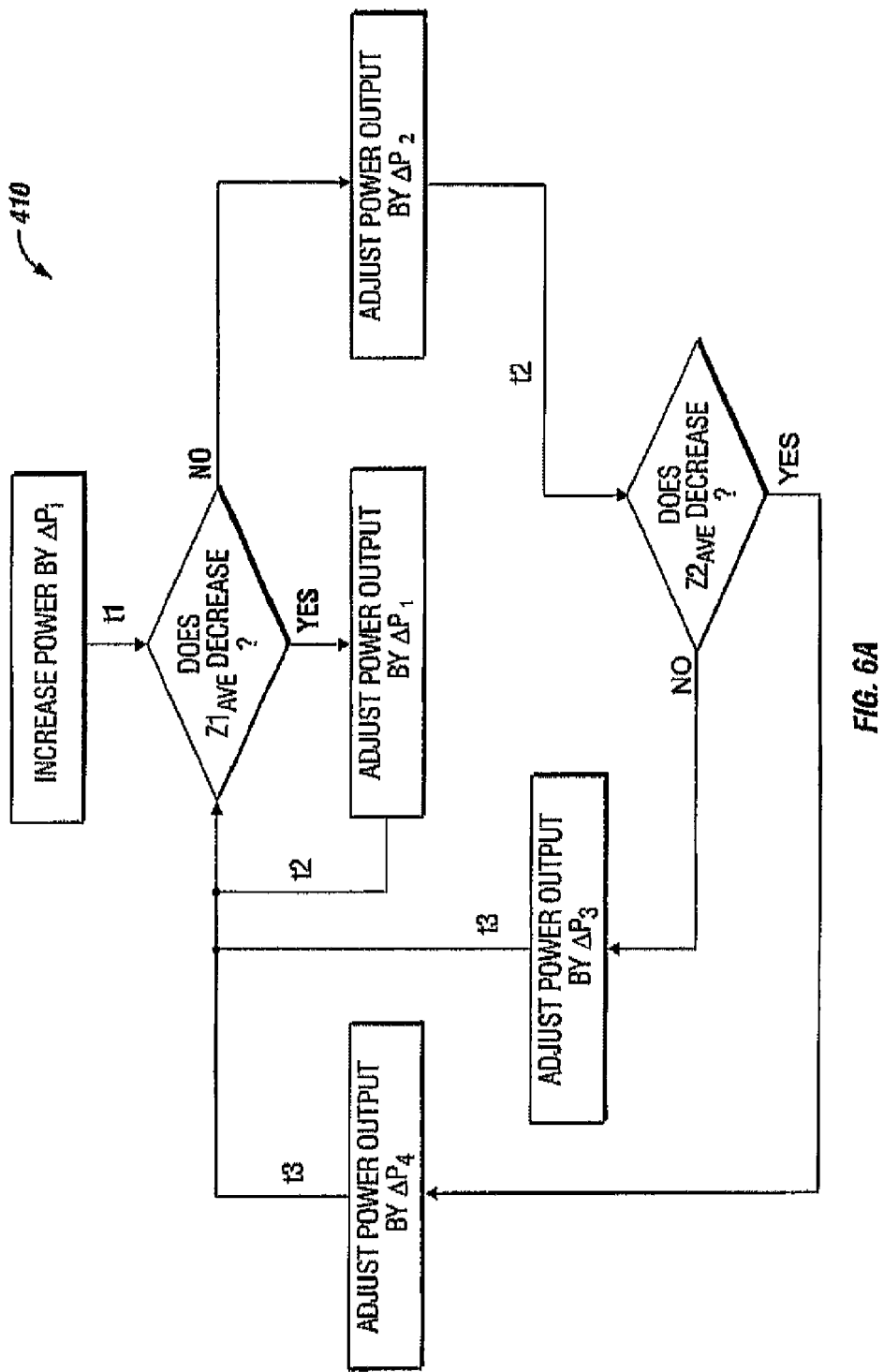
FIG. 6A is a schematic block diagram of a normal priority task algorithm according to embodiments of the present disclosure.

FIG. 6A shows a normal priority task 410 controlled by the inner loop control module 402 for automatic power adjustment to achieve peak conductance. The normal priority task 410 adjusts the power output by the generator 20 to continuously achieve peak tissue conductance (i.e., lowest tissue impedance) irrespective of changes to tissue (e.g., thickness, bubble formation, temperature, etc.), variations in generator output (e.g., manual adjustment of generator output power), and device and/or accessory selection (e.g., monopolar device, bipolar forceps, etc.). The inner loop control module 402 utilizes the normal priority task 410 to continuously monitor average tissue impedance over a period of time (e.g., a $dZ_{AVE}/dt$ waveform) as an indicator of tissue conductance since tissue conductance is inversely proportional to tissue impedance. The module 402 then automatically adjusts the output power of the generator 20 to provide the lowest possible tissue impedance and, thus, the highest possible tissue conductance. The normal priority task 410 is characterized by a dual-control loop that continuously interrogates (e.g., via the sensor module 22) the slope of the average impedance waveform over a particular window of time and adjusts the output power of the generator 20 in response to the direction of the slope (e.g., m=0, m<0, or m>0) detected over the duration of that particular window of time.

During operation of the normal priority task 410, an initial increase of the output power of the generator 20 is made over the duration of a first sample window of time (e.g., a user-defined time delay). During the first sample window of time, the sensor module 22 determines a first slope of the average impedance waveform in response to the initial increase in output power of the generator 20. During a second sample window of time, a second adjustment is made to the power output by the generator 20 and a second slope of the average impedance waveform is determined. If the second slope of the average impedance waveform is substantially the same as the first slope of the average impedance waveform, a third adjustment to the output power of the generator 20 is made. In this scenario, the second adjustment made to the power output by the generator 20 is a "reverse" adjustment to that of the first adjustment made to the power output by the generator 20.

During a first sampled time delay "t1," the tissue ablation procedure is activated (e.g., by pressing of a foot pedal or handswitch) and a host processor (e.g., microprocessor 5) activates the normal priority task 410 to monitor changes in average impedance as a function of time (e.g., dz/dt). More specifically, an initial increase $\Delta P_i$ in output power of the generator 20 is made during time delay t1 while the sensor module 22 continuously monitors a first sampled average tissue impedance $Z1_{AVE}$ to detect changes therein in response to the initial increase $\Delta P_i$ in output power of the generator 20 as a function of time delay t1. The change in $Z1_{AVE}$ may be embodied as a waveform interpreted by the inner loop control module 402 which represents the first average impedance $Z1_{AVE}$ as a function of time delay t1 (e.g., $dZ1_{AVE}/dt1$). In this manner, the normal priority task 410 may monitor the slope of the impedance waveform as an indication of changes in average tissue impedance over a sample window of time.

In embodiments, time delay t1 may be up to four (4) seconds during which the initial increase $\Delta P_i$ in output power of the generator 20 is made at a rate of twenty (20) watts per second. In this configuration, the output power of the generator 20 may be gradually increased to eighty watts (80) over the duration of the time delay t1.

If, over the duration of the first time delay t1, the first average impedance $Z1_{AVE}$ decreases (e.g., the slope of $dZ1_{AVE}/dt1<0$) in response to the initial increase $\Delta P_i$ in power output, the controller 24 makes a first adjustment $\Delta P_1$ to increase the power output over the duration of a second time delay "t2." In certain embodiments, the second time delay t2 may be up to four (4) seconds to allow the sensor module 22 to record a sufficient sample of data related to changes in tissue impedance.

Conversely, if over the duration of the first time delay t1, the first average tissue impedance $Z1_{AVE}$ either increases or is unchanged (e.g., the slope of $dZ1_{AVE}/dt1>0$) in response to the initial increase $\Delta P_i$ in power output, the controller 24 makes a second adjustment $\Delta P_2$ to decrease the power output over the duration of the second time delay t2.

As the controller 24 makes the second adjustment $\Delta P_2$ to decrease the power output over the duration of the second time delay t2, the sensor module 22 continuously monitors for changes in a second sampled average tissue impedance $Z2_{AVE}$. In embodiments, the second adjustment $\Delta P_2$ may be as much as a five (5) watt decrease over the duration of the second time delay t2. If, over the duration of the second time delay t2, the second average tissue impedance $Z2_{AVE}$ either increases or is unchanged (e.g., the slope of $dZ2_{AVE}/dt2>0$) in response to the second adjustment $\Delta P_2$ to decrease the power output, the controller 24 makes a third adjustment $\Delta P_3$ to increase the power output by the generator 20 over the duration of a third time delay "t3." The normal priority task 410 is thereafter repeated. If, over the duration of the second time delay t2, the second average tissue impedance $Z2_{AVE}$ decreases (e.g., the slope of $dZ2_{AVE}/dt2>0$) in response to the second adjustment $\Delta P_2$ to decrease the power output, the controller 24 makes a fourth adjustment $\Delta P_4$ to decrease the power output over the duration of the third time delay t3, and the normal priority task 410 is repeated.

In this way, the normal priority task 410 performs a reverse adjustment of power output by the generator 20 over the duration of the third time delay t3 relative to the adjustment made over the duration of the second time delay t2 in response to the same direction of the change (e.g., same slope direction) in the average tissue impedance as detected by the controller 24 during the first time delay t1. That is, over the duration of the first time delay t1, if the first average tissue impedance $Z1_{AVE}$ either increases or is unchanged in response to the initial increase $\Delta P_i$ in power output the controller 24 makes the second adjustment $\Delta P_2$ to decrease the power output over the duration of the second time delay t2. Conversely, if the second average tissue impedance $Z2_{AVE}$ either increases or is unchanged in response to the second adjustment $\Delta P_2$ to decrease the power output the controller 24 makes the third adjustment $\Delta P_3$ to increase the power output over the duration of the third time delay t3. It is in this manner that the normal priority task 410 operates to control the power output by the generator 20 to achieve the highest possible tissue conductance and, thus, the lowest possible tissue impedance throughout the duration of a given procedure.

In embodiments, the duration of the time delays t1, t2, t3, the amount of the power adjustments $\Delta P_i$, $\Delta P_1$, $\Delta P_2$, $\Delta P_3$, $\Delta P_4$, the rate at which the power adjustments $\Delta P_1$, $\Delta P_1$, $\Delta P_2$, $\Delta P_3$, $\Delta P_4$ are made, and the maximum level to which the power output may be increased by $\Delta P_i$ may be pre-determined by the user via the user inputs of the generator 20 and/or a software-based user interface, as will be discussed in further detail below.

The outer loop control module 404 is layered over the inner loop control module 402 and runs concurrently therewith to provide additional control of the generator 20 to reach a desired output value or effect. The outer loop control module 404 utilizes a high priority task 420 to prevent tissue properties (e.g., impedance) from rising and/or falling outside the peak conductance range or a so-called "run-away state." Upon activation, the sensor module 22 records a baseline impedance value. $Z_{BASE}$ and transmits this value to the controller 24 for storing in the memory 26. The high priority task 420 processes the base impedance $Z_{BASE}$ stored in the memory 26 and continually monitors deviations in average tissue impedance $Z_{AVE}$ from the base impedance $Z_{BASE}$ as a function of time (e.g., a dz/dt waveform). The high priority task 420 compares the deviations to a threshold impedance value $Z_{MAX}$, and automatically adjusts the output power of the generator 20 to counteract increases in the average impedance $Z_{AVE}$ that breach the threshold value $Z_{MAX}$. That is, if a rise in average tissue impedance $Z_{AVE}$ over a sample window of time exceeds the threshold value $Z_{MAX}$, the output power of the generator 20 is decreased by the controller 24. In embodiments, the threshold impedance value $Z_{MAX}$ may be determined by detecting a change in average impedance $Z_{AVE}$ over some period of time (e.g., an average change of 20 ohms over seven seconds), and comparing this change in average impedance $Z_{AVE}$ to the base impedance value $Z_{BASE}$ stored in memory 26.

Figure 6B:
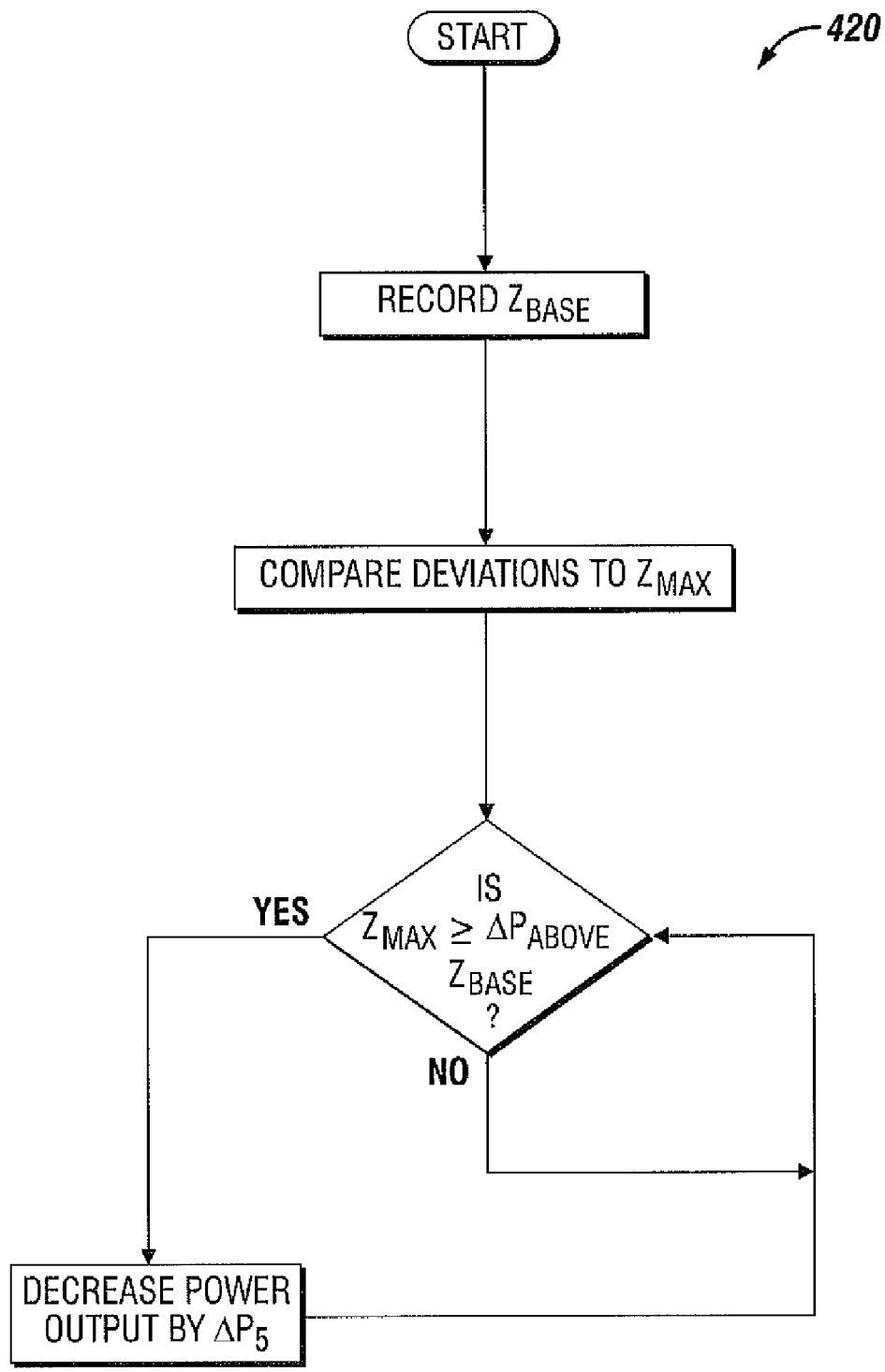
FIG. 6B is a schematic block diagram of a high priority task algorithm according to embodiments of the present disclosure.

FIG. 6B shows the high priority task 420 controlled by the outer loop control module 404 for automatic power adjustment based on detected rises in average tissue impedance $Z_{AVE}$ that exceed the threshold impedance value $Z_{MAX}$. The high priority task 420 is layered over the normal priority task 410 and runs concurrently therewith. Specifically, the outer loop control module 404 utilizes the high priority task 420 to continuously monitor average tissue impedance as a function of time (e.g., a dz/dt waveform). The average tissue impedance may be an average peak impedance $Z_{PEAK}$ sampled over a substantially short period of time, e.g., 0.05 seconds. If the rise in peak impedance $Z_{PEAK}$ exceeds or is equal to a predetermined impedance value $\Delta P$ (e.g., 20 ohms nominal) above the base impedance $Z_{BASE}$, the controller 24 makes a fifth adjustment $\Delta P_5$ to decrease the power output.

In embodiments, the output level of the generator 20 at which the base impedance $Z_{BASE}$ will be determined, the impedance value $\Delta P$, and the fifth adjustment $\Delta P_5$ may be pre-determined by the user via the user inputs of the generator 20 and/or a software-based user interface, as will be discussed in further detail below.

In embodiments, the outer loop control module 404 may utilize a low priority task 430 to determine when to terminate the power output by the generator 20 to end a given tissue treatment. The low priority task 430 is based on a determination that an equilibrium exists between the energy applied by the generator 20 (e.g., via the forceps 10) and the energy that is dissipated from the tissue site. The low priority task 430 may determine whether average tissue impedance has achieved its lowest sustainable level and remains at that level without substantial change for a substantial period of time.

Figure 6C:
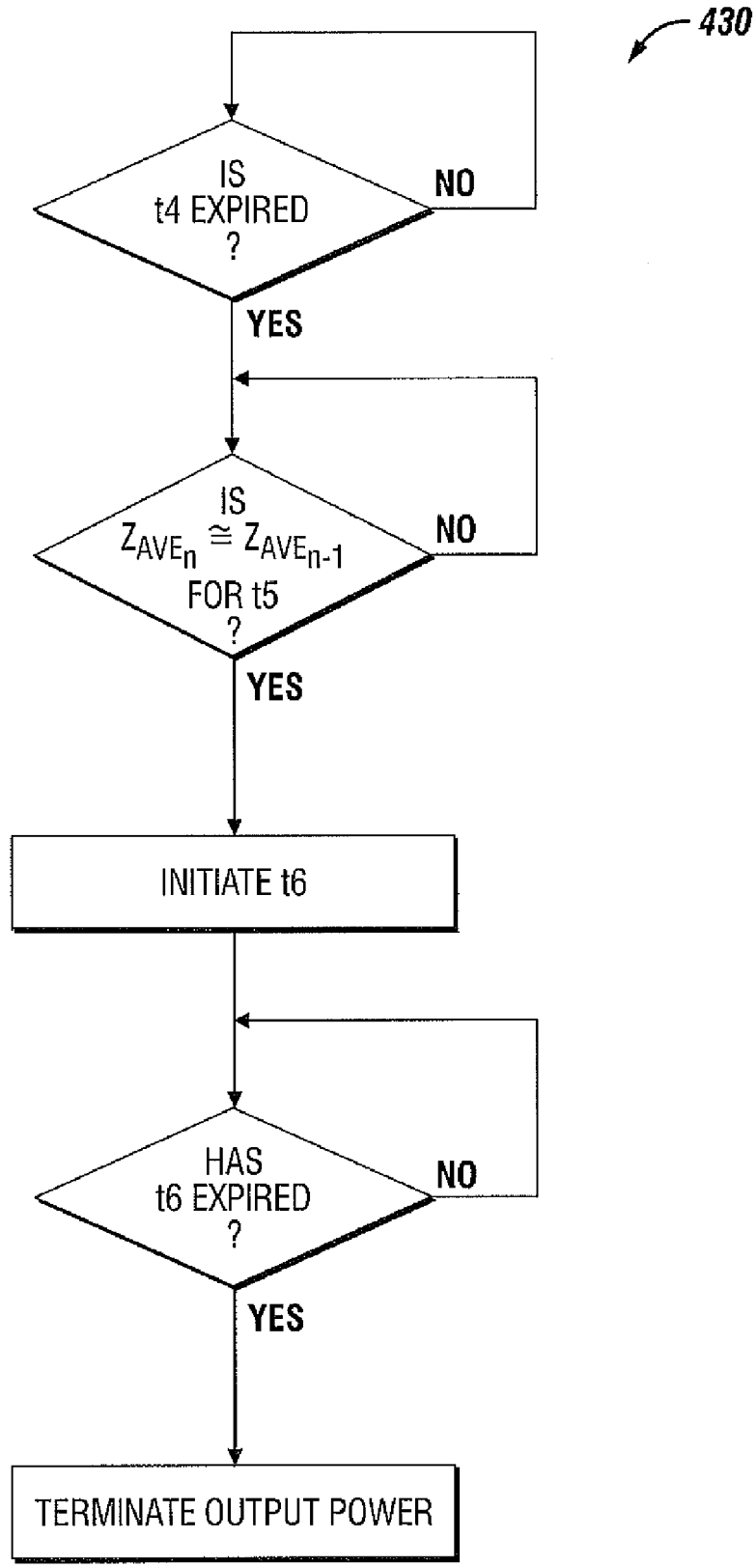
FIG. 6C is a schematic block diagram of a low priority task algorithm according to embodiments of the present disclosure.

Discussed below with reference to FIG. 6C, the low priority task 430 is layered over the normal priority task 410 and runs concurrently therewith. The outer loop control module 404 utilizes the low priority task 430 to continuously monitor average tissue impedance as a function of time (e.g., over the duration of a given procedure) Specifically, the controller 24 continually receives a current average tissue impedance value $Z_{AVEn}$ from the sensor module 22. Upon processing the current average tissue impedance value $Z_{AVEn}$, the low priority task 430 compares the current tissue impedance value $Z_{AVEn}$ to a historical tissue impedance value $Z_{AVEn-1}$ stored in the memory 26 from the previous iteration through the low priority task 430. Thereafter, the current average tissue impedance value $Z_{AVEn}$ is stored in the memory 26 as the historical tissue impedance Value $Z_{AVEn-1}$. In operation, after the expiration of a fourth time delay "t4" following the activation of the generator 20, the low priority task 430 monitors average tissue impedance for certain criteria that may indicate that a given treatment is complete and, thus, the power output may be terminated. In certain embodiments of the present disclosure, this criteria may include determining that the current tissue impedance value $Z_{AVEn}$ is substantially equivalent to the historical tissue impedance value $Z_{AVEn-1}$ stored in the memory 26 over the duration of a fifth time delay "t5" after the generator 20 is activated. In response, the generator 20 may continue to output power over the duration of a sixth time delay "t6." Following the time delay t6, the generator 20 is turned "off" and the procedure is terminated. In certain embodiments of the low priority task 430, the power output may be terminated immediately by the controller 24 upon the expiration of the fifth time delay t5. Alternatively, output may be adjusted by the controller 24 to a predetermined level by the user (e.g., via the user inputs of the generator 20 and/or a software-based user interface).

In embodiments, the duration of the time delays t4, t5, t6 may be pre-determined by the user via the user inputs of the generator 20 and/or a software-based user interface, as will be discussed in further detail below.

Figure 7A:
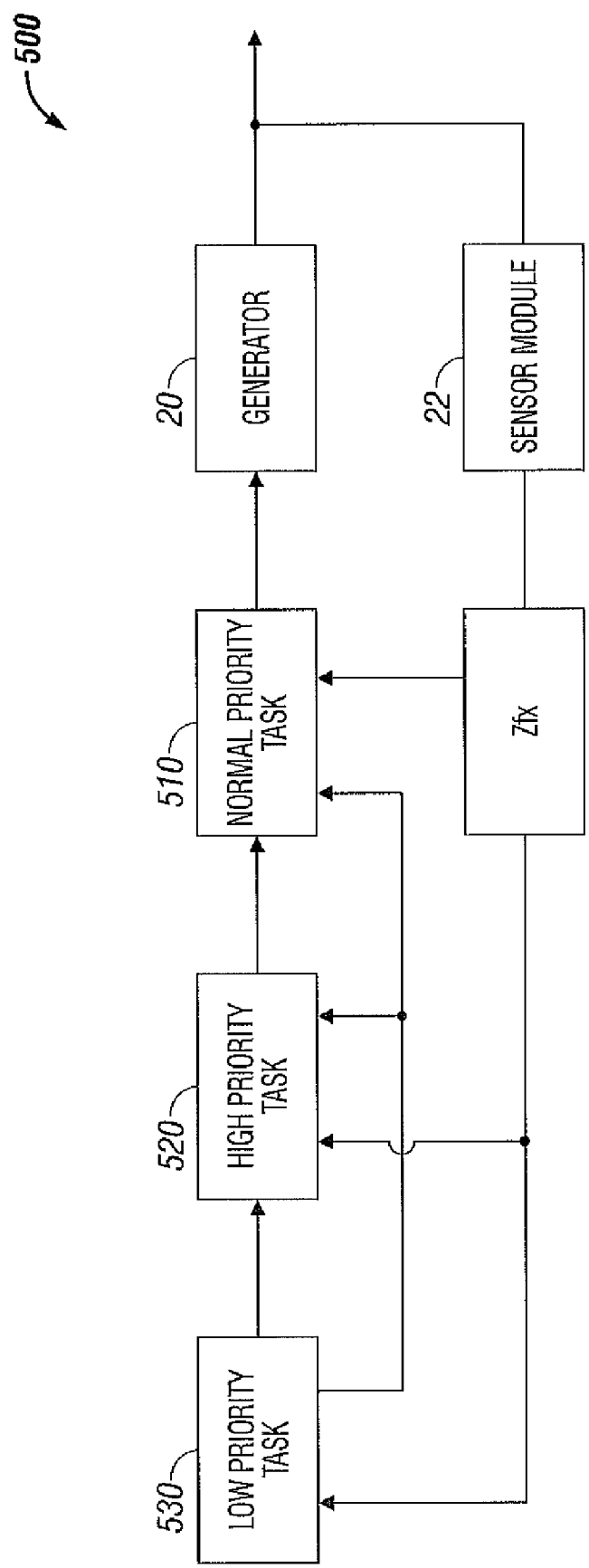
FIG. 7A is a schematic block diagram of a software system for use with the generator of FIG. 2.

According to embodiments of the present disclosure, the interrogation of impedance may be achieved via single pole recursive filtering. FIG. 7A illustrates a software system 500 embedded in the memory 26 and executed by the microprocessor 25 which utilizes a normal priority task 510, a high priority task 520, and low priority task 530 to control generator 20 output based on changes in average tissue impedance as a function of time. Each task 510, 520, 530 processes averaged impedance data received from a plurality of single pole recursive impedance filters that continuously filter and/or average tissue impedance data sensed by the sensor module 22.

In the illustrated embodiment, eight impedance filters Zf1-Zf8 are used in conjunction with the software system 500. Each of the impedance filters Zf1-Zf8 may be formatted for use with the following data averaging formula (1):

$$ZfX_n = Zin*A + ZfX_{n-1}*B \qquad (1)$$

A and B are dependent on a time constant and may be specified by the user, via the input controls of the generator 20, for each particular impedance filter Zfx. When calculating A and B, the following formulas may be used:

$$B = e^\wedge(-1/\text{number of samples});$$

$$A = 1-B.$$

The sample rate may also be specified by the user for calculating the number of samples. In formula (1), Zin is the new impedance value (e.g., $Z_{RMS}$) just calculated, and $ZfX_{n-1}$ is the filtered impedance, for the filter number specified by X, from the previous iteration through the loop, and $ZfX_n$ is the new filtered impedance value for the filter number specified by X.

Figure 7B:
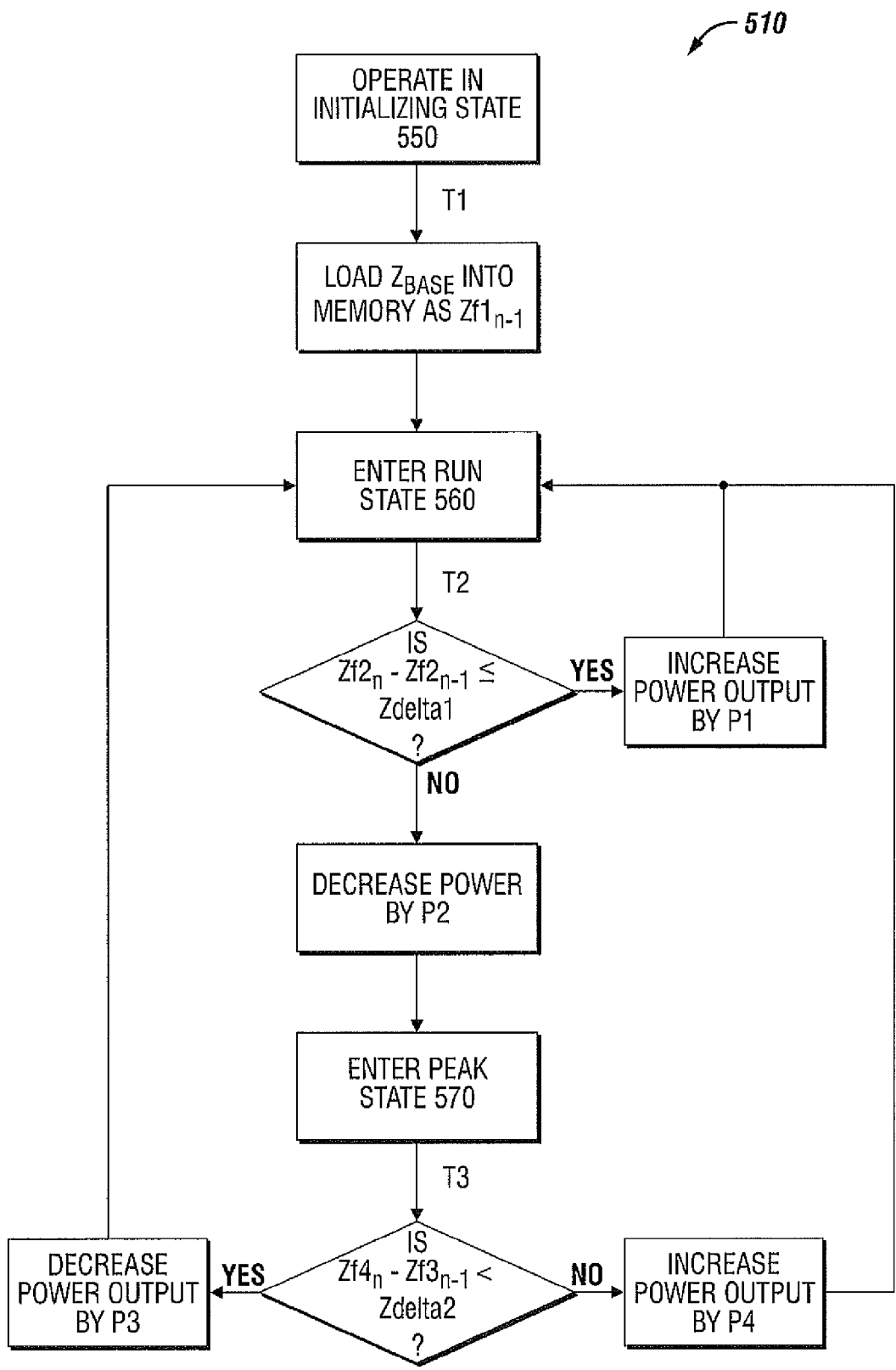
FIG. 7B is a schematic block diagram of a normal priority task algorithm for use with the software system of FIG. 7A.

Referring now to FIG. 7B, the normal priority task 510 is made up of three states, namely, an initializing state 550, a run state 560, and a peak state 570. During the initializing state 550, the ablation procedure is activated (e.g., by pressing of a foot pedal or handswitch) and a host processor (e.g., microprocessor 5) activates the software system 500 for monitoring the plurality of impedance filters Zf1-Zf8. Upon activation of the state 550, a first timer "T1" is initialized to run concurrently with the initializing state 550. The first timer T1 may be set by the user (e.g., via the user inputs of the generator 20 and/or a software-based user interface) as the amount of time the software system 500 waits during the state 550, after initial activation, before interrogating the plurality of impedance filters, as will be discussed in further detail below.

Once turned on, the generator 20 operates at a baseline level of power $P_{BASE}$. It is at this baseline level of power $P_{BASE}$ that the sensor module 22 records a baseline impedance $Z_{BASE}$ and transmits this value to the controller 24 for storing in the memory 26. Once the baseline impedance $Z_{BASE}$ has been recorded, the power output by the generator 20 is ramped by the controller 24 to an initial level $P_{INIT}$. The user may be able to specify (e.g., via the user inputs of the generator 20 and/or a software-based user interface) the rate at which the power output by the generator 20 is ramped as well as a maximum level of power $P_{MAX}$ to which the generator 20 may be ramped. The power output by the generator 20 is ramped by the controller 24 until either the first timer T1 expires or $P_{MAX}$ is reached.

Upon expiration of the first timer Ti, the normal priority task 510 stores the baseline impedance $Z_{BASE}$ into the memory 26 as impedance value $Zf1_{n-1}$ and enters the run state 560. Once the run state 560 is initialized, the normal priority task 510 starts a second timer "T2" which runs concurrently with the run state 560. The second timer T2 may be predetermined by the user (e.g., via the user inputs of the generator 20 and/or a software-based user interface) as the amount of time the normal priority task 510 operates in the run state 560 prior to interrogating the plurality of impedance filters for average impedance data.

If the run state 560 is entered from the initializing state 550, the software system 500 immediately calculates the difference between the current filtered impedance $Zf2_n$ and the previous filtered impedance $Zf1_{n-1}$ and compares this difference to a first impedance reference Zdelta1. The first impedance reference, Zdelta1, is the amount of change from the previous filtered impedance $Zf1_{n-1}$ to the current filtered impedance $Zf2_n$ which is a threshold for triggering an increase or decrease in power output by the generator 20. The impedance reference Zdelta1 may be predetermined (e.g., via the user inputs of the generator 20 and/or a software-based user interface) by the user.

If the difference between the current filtered impedance $Zf2_n$ and the previous filtered impedance $Zf1_{n-1}$ is less than or equal to Zdelta1, the controller 24 makes a first adjustment P1 to increase the power output by the generator 20 and the normal priority task 510 reenters the run state 560. Upon reentering the run state 560, the software system 500 restarts the second timer T2 and waits for the second timer to expire before interrogating impedance filters Zf1 and Zf2 for filtered impedance data.

If the difference between the current filtered impedance $Zf2_n$ and the previous filtered impedance $Zf1_{n-1}$ is greater than Zdelta1, the controller 24 makes a second adjustment P2 to decrease the power output by the generator 20 and the normal priority task 510 enters the peak state 570. Upon entering the peak state 570, the software system 500 starts a third timer "T3", as will be discussed in further detail below.

In embodiments, the duration of the third timer T3, the amount of the first and second power adjustments P1, P2 may be pre-determined by the user via the user inputs of the generator 20 and/or a software-based user interface, as will be discussed in further detail below.

Upon exiting the run state 560, the software system 500 stores the current filtered impedance value $Zf1_n$ into the memory 26 as the previous filtered impedance $Zf1_{n-1}$ and stores the filtered impedance $Zf3n$ into the memory 26 as the previous filtered impedance $Zf3_{n-1}$. That is, prior to the exiting of the run state 560, the current filtered impedances $Zf1_n$ and $Zf3_n$ determined during the present iteration through the run state 560 become the respective previous filtered impedances $Zf1_{n-1}$ and $Zf3_{n-1}$ once the run state 560 is reentered (i.e., once the present iteration through the run state 560 becomes the previous iteration through the run state).

The third timer T3 is initialized by the software system 500 to coincide with the initialization of the peak state 570 and to run concurrently therewith. Once the third timer T3 expires, the software system 500 calculates the difference between the current filtered impedance $Zf4_n$ and the previous filtered impedance $Zf3_{n-1}$ and compares this difference to a second impedance reference Zdelta2. The second impedance reference, Zdelta2, is the amount of change from the previous filtered impedance $Zf3_{n-1}$ to the current filtered impedance $Zf4_n$ which is a threshold fro triggering an increase or decrease in power output.

If the difference between the current filtered impedance $Zf4_n$ and the previous filtered impedance $Zf3_{n-1}$ is less than the second impedance reference Zdelta2, the controller 24 makes a third adjustment P3 to decrease the power output and the normal priority task 510 reenters the run state 560 and the software system 500 restarts the second timer T2.

If the difference between the current filtered impedance $Zf4_n$ and the previous filtered impedance $Zf3_{n-1}$ is greater than or equal to the second impedance reference Zdelta2, the controller 24 makes a fourth adjustment P4 to increase the power output and the normal priority task 510 reenters the run state 560 and the software system 500 restarts the second timer T2.

In embodiments, the second impedance reference Zdelta2 and the third and fourth power adjustments P3, P4 may be pre-determined by the user via the user inputs of the generator 20 and/or a software-based user interface, as will be discussed in further detail below.

Upon exiting the peak state 570, the software system 500 stores the current filtered impedance $Zf1_n$ into the memory 26 as the previous filtered impedance $Zf1_{n-1}$ and stores the current filtered impedance $Zf3_n$ into the memory 26 as the previous filtered impedance $Zf3_{n-1}$.

In embodiments, the duration of the first, second, and third timers T1, T2, T3 and the amount of the first and second power adjustments P1, P2 may be pre-determined by the user via the user inputs of the generator 20 and/or a software-based user interface, as will be discussed in further detail below.

Figure 7C:
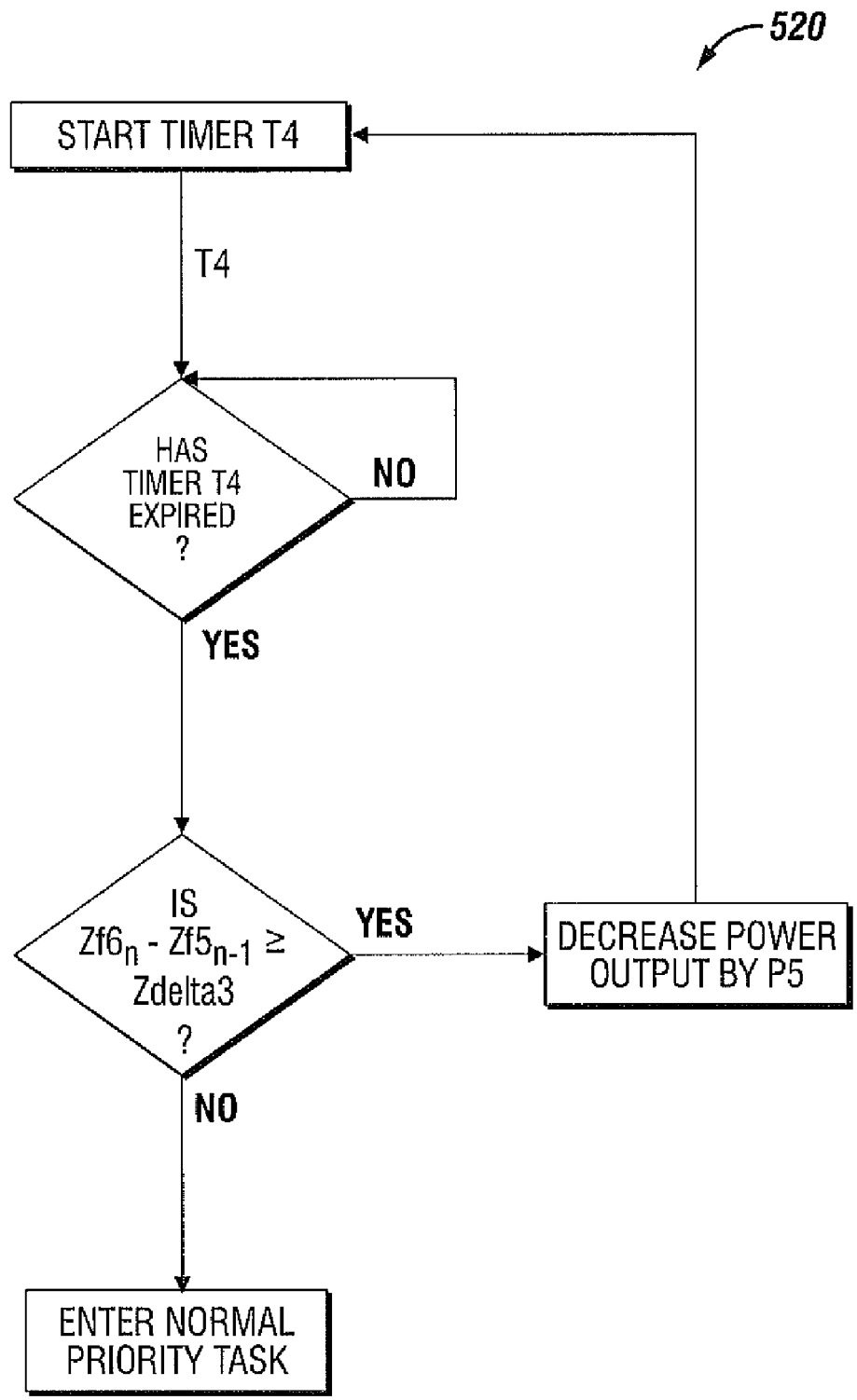
FIGS. 7C is a schematic block diagram of a high priority task algorithm for use with the software system of FIG. 7A.
Figure 7D:
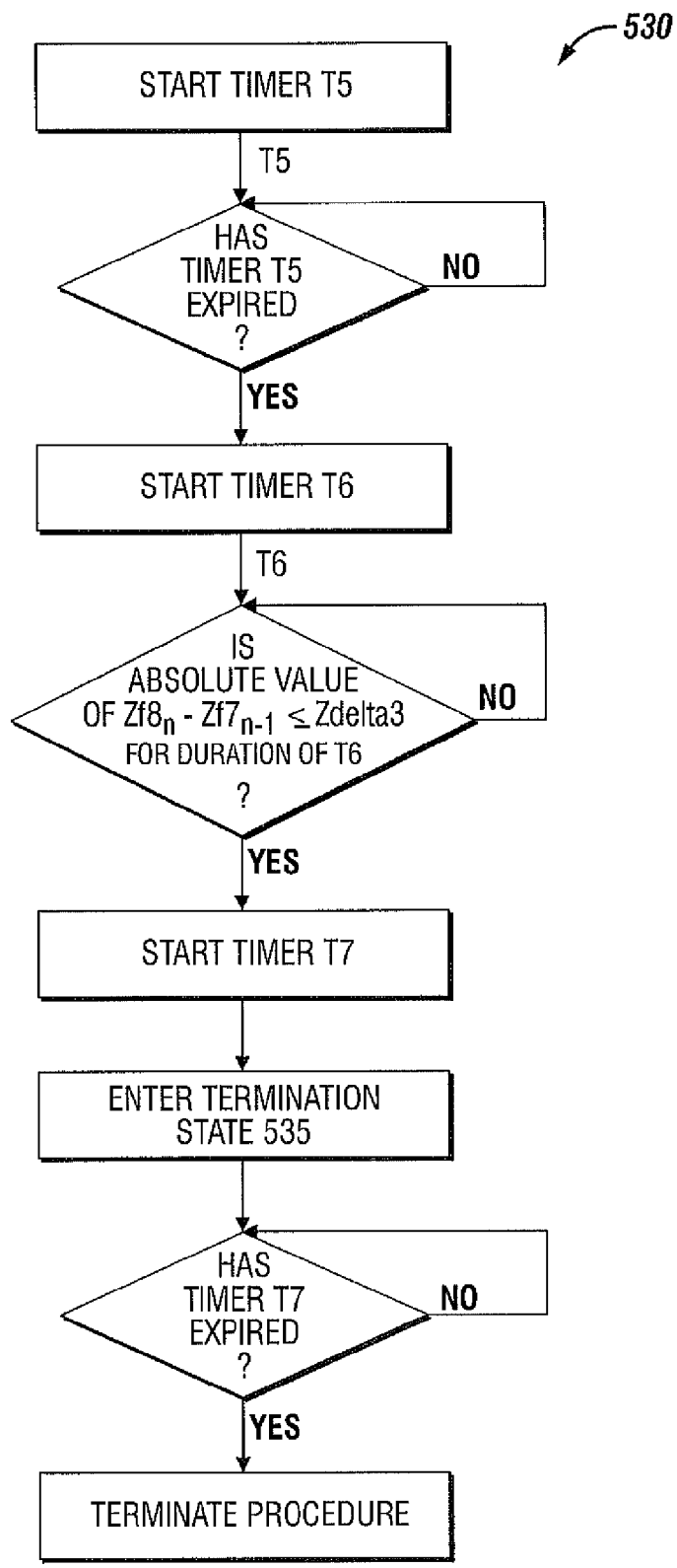
FIG. 7D is a schematic block diagram of a normal priority task algorithm for use with the software system of FIG. 7A.

Referring now to FIG. 7C, the high priority task 520 is layered over the normal priority task 510 and runs concurrently therewith to provide additional control of the generator 20 to reach a desired output value or effect. A fourth timer "T4" is initialized by the software system 500 to coincide with the initialization of the high priority task 520 and to run concurrently therewith. Once the fourth timer T4 expires, the software system 500 calculates the difference between the current filtered impedance $Zf6_n$ and the current filtered impedance $Zf5_n$ and compares this difference to a third impedance reference Zdelta3. The third impedance reference, Zdelta3, is the amount of change from the current filtered impedance $Zf5_n$ to the current filtered impedance $Zf6_n$ which is a threshold for triggering a decrease in power output. In this manner, the third impedance reference Zdelta3 operates in a threshold capacity to prevent dangerous conditions such as a run-away state that may arise and lead to continued power increases and impedance rises.

If the difference between the current filtered impedance $Zf6_n$ and the current filtered impedance $Zf5_n$ is greater than or equal to the third impedance reference Zdelta3, the controller 24 makes a fifth adjustment P5 to decrease the power output and the software system 500 reenters the high priority task 520 and restarts the fourth timer T4.

If the difference between the current filtered impedance $Zf6_n$ and the current filtered impedance $Zf5_n$ is less than the third impedance reference Zdelta3, the software system 500 enters the normal priority task 510. Hence, the normal priority task 510 is only entered from the high priority task 520 if the third reference impedance Zdelta3 threshold is not equaled or exceeded.

In embodiments, the duration of the fourth timer T4, the third impedance reference Zdelta3, and the amount of the fifth power adjustment P5 may be pre-determined by the user via the user inputs of the generator 20 and/or a software-based user interface, as will be discussed in further detail below.

The low priority task 530 is layered over the normal priority task 510 and runs concurrently with both the high priority task 520 and the normal priority task 510 to provide additional control of the generator 20 to terminate the procedure once a desired output value or effect has been achieved. A fifth timer "T5" is initialized to coincide with the initialization of the vessel sealing procedure (e.g., by pressing a foot pedal or handswitch), and to run concurrently therewith. Once the fifth timer T5 expires, the software system 500 continuously interrogates whether particular impedance conditions indicative of a desired tissue effect exist for the duration of a sixth timer "T6" and, if such criteria is met, accordingly initiates a process to terminate the power output. Specifically, the software system 500 calculates the difference between the current filtered impedance $Zf8_n$ and the current filtered impedance $Zf7_n$ and compares this difference to a fourth impedance reference Zdelta4. The fourth impedance reference Zdelta4 is the amount of change from the current filtered impedance $Zf7_n$ to the current filtered impedance $Zf8_n$ that initiates a seventh timer "T7," the expiration of which triggers the generator 20 to shut off and the procedure to be terminated.

If the absolute value of the difference between the current filtered impedance $Zf8_n$ and the current filtered impedance $Zf7_n$ is less than or equal to the impedance reference Zdelta3 for the duration of the sixth timer T6, the seventh timer T7 is initialized. In addition, a termination state 535 of the low priority task 530 is triggered to provide for a plurality of options which allow the user to predetermine (e.g., via the user inputs of the generator 20) how the generator 20 will behave once the condition discussed above is satisfied for the duration of the sixth timer T6. Options available to the user with respect to the termination state 535 may include allowing the generator 20 to operate at it's current output level for the duration of the seventh timer T7, specifying an output level at which generator 20 is to operate for the duration of the seventh timer T7, and continuing with the low priority task 530 until the seventh timer T7 expires.

If the absolute value of the difference between the current filtered impedance $Zf8_n$ and the current filtered impedance $Zf7_n$ is not less than or equal to the impedance reference Zdelta3 for the duration of the sixth timer T6, the software system 500 continues to execute the low priority task 530 concurrently with the high priority and normal priority tasks 520 and 530.

In embodiments, the duration of the fifth, sixth, and seventh timers T5, T6, T7 and the fourth impedance reference Zdelta4 may be pre-determined by the user via the user inputs of the generator 20 and/or a software-based user interface, as will be discussed in further detail below.

In embodiments of the present disclosure, an eighth timer T8 may be specified by the user (e.g., via the user inputs of the generator 20 and/or a software-based user interface) as a "master" timer (i.e., total procedure time) for the operation of the generator 20 in a given procedure. In this configuration, the generator 20 is shut off upon the expiration of the procedure timer T8 regardless of whether or not the termination state 535 is entered.

Figure 8:
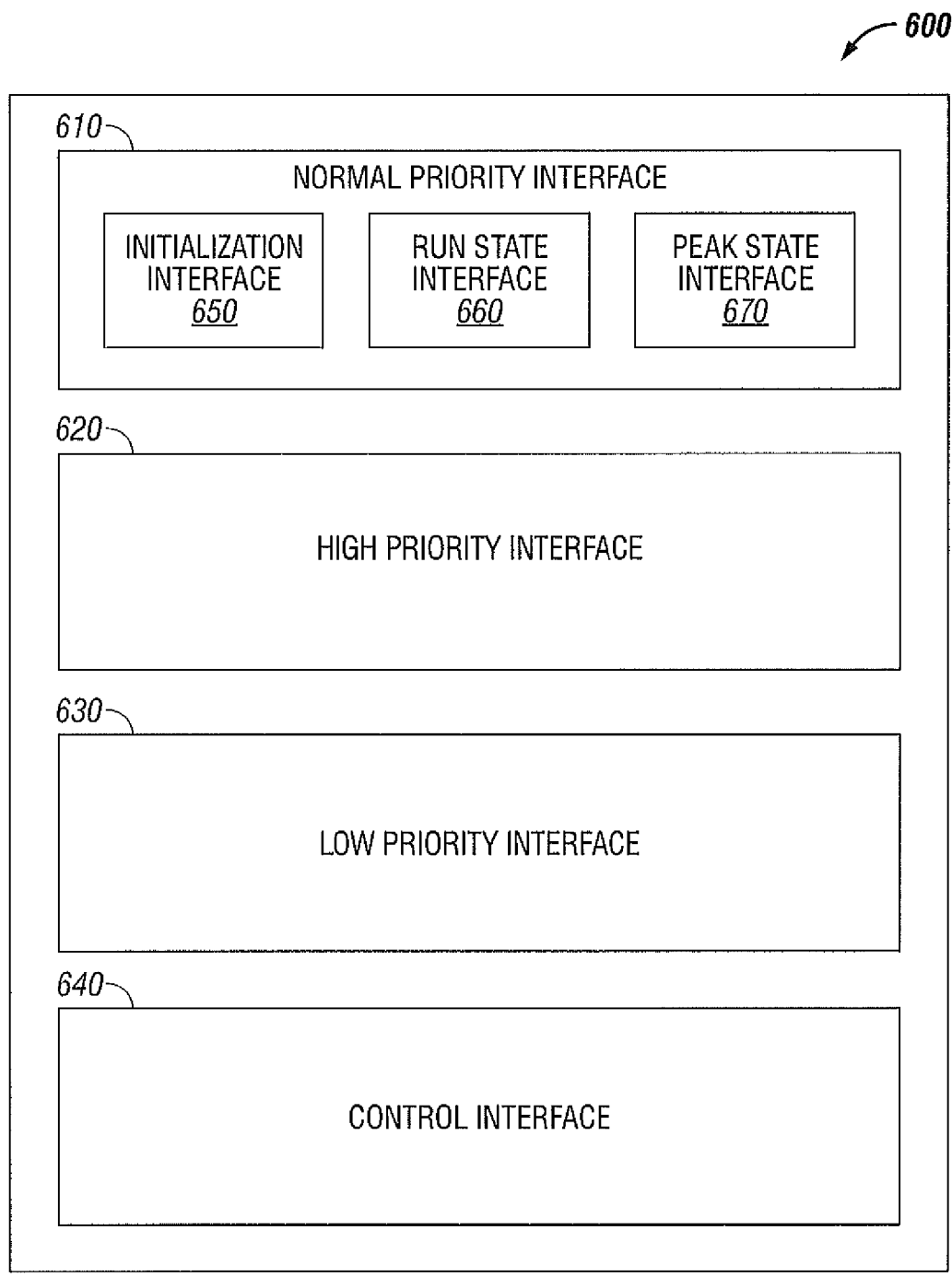
FIG. 8 is a schematic block diagram of a user interface for use with the generator and software system according to embodiments of the present disclosure.

With reference now to FIG. 8, a software-based graphical user interface 600 is shown for use with embodiments of the software system 500 of the present disclosure. The interface 600 may include a plurality of editable parameters to allow the user to provide specific values (e.g., via the user inputs of the generator 20) for controlling the power output by the generator 20 via the software system 500. The interface 600 allows the user to test and/or validate the software system 500 of the present disclosure. Specifically, the interface 600 may be organized by priority level and/or task level including a normal priority interface 610, a high priority interface 620, and a low priority interface 630, as shown in FIG. 8. Further, a control interface 640 may be provided to allow the user to specify various control parameters such as, for example, the procedure time (e.g., the eighth timer T8) and the file path and/or location of a file to be executed by the software system 500, etc.

The normal priority interface 610 is configured to be edited by the user to provide specific parameters for predetermining the behavior of the normal priority task 510 during a given procedure. The normal priority interface 610 may be divided into three sub-interfaces, namely, an initialization state interface 650, a run state interface 660, and a peak state interface 670, to coincide with the three states 550, 560, and 570 of the normal priority task 510, respectively. The interfaces 650, 660, and 670 may be edited by the user to provide specific parameters for further predetermining the behavior of the normal priority task 510 during a given procedure.

Referring now to interface 650, the user may be able to specify parameters related to the initialization state 550 of the normal priority task 510, such as the duration of the first timer T1 and power levels of $P_{BASE}$, $P_{INIT}$, $P_{RATE}$, and $P_{MAX}$. With reference to interface 660, the user may be able to specify parameters related to the run state 560 of the normal priority task 510, such as the duration of the second timer T2, the first impedance reference Zdelta1, and the amount of the first and second power adjustments P1, P2. With reference to interface 670, the user may be able to specify parameters related to the peak state 570 of the normal priority task 510, such as the duration of the third timer T3, the second impedance reference Zdelta2, and the amount of the third and fourth power adjustments P3 and P4.

The high priority interface 620 is configured to be edited by the user to provide specific parameters for predetermining the behavior of the high priority task 520 during a given procedure. In particular, the user may be able to specify parameters such as the duration of the fourth timer T4, the third impedance reference Zdelta3, and the fifth power adjustment P5.

The low priority interface 630 is configured to be edited by the user to provide specific parameters for predetermining the behavior of the low priority task 530 during a given procedure. In particular, the user may be able to specify parameters such as the duration of the fifth, sixth, and seventh timers T5, T6, T7 and impedance reference Zdelta4. Further, with respect to the termination state 535 of the low priority task 530, the user may be able to choose from a menu of options (not explicitly shown) to select how the generator 20 will behave over the duration of the seventh timer T7 once the termination state 535 is entered (e.g., continue current output level, adjust to a predetermined output level, shut off upon the expiration of the seventh timer T7, etc.).

While several embodiments of the disclosure have been shown in the drawings and/or discussed herein, it is not intended that the disclosure be limited thereto, as it is intended that the disclosure be as broad in scope as the art will allow and that the specification be read likewise. Therefore, the above description should not be construed as limiting, but merely as exemplifications of particular embodiments. Those skilled in the art will envision other modifications within the scope and spirit of the claims appended hereto.

What is claimed is:

1. A method for controlling an electrosurgical waveform generated by an electrosurgical generator comprising the steps of:
   activating an electrosurgical generator to produce an electrosurgical waveform;
   increasing power of the electrosurgical waveform during a first sample window;
   determining a direction of change in a first average impedance during the first sample window in response to the increase in power of the electrosurgical waveform;
   performing a first adjustment of power of the electrosurgical waveform in response to the direction of change in the first average impedance during a subsequent sample window;
   determining a direction of change in a subsequent average impedance during the subsequent sample window in response to the first adjustment of power; and
   performing a subsequent adjustment of power of the electrosurgical waveform in response to the direction of change in the subsequent average impedance, wherein the subsequent adjustment of power is reverse to that of the first adjustment of power when the direction of change in the first and subsequent average impedances is the same.

2. A method according to claim 1, wherein the step of adjusting power further comprises the steps of:
   increasing the power of the electrosurgical waveform in response to a decrease in the first average impedance curve; and
   decreasing the power of the electrosurgical waveform in response to an increase in the average impedance.

3. A method according to claim 1, wherein the step of performing a subsequent adjustment of power further comprises the steps of:
   decreasing the power of the electrosurgical waveform in response to a decrease in the first average impedance; and
   increasing the power of the electrosurgical waveform in response to an increase in the average impedance.

4. A method according to claim 1, wherein after the step of performing a subsequent adjustment of power, the method further comprises the steps of:
   continuously measuring peak impedance during a third sample window; and
   comparing the peak impedance to a predetermined threshold change in impedance to determine a rapid rise in impedance.

5. A method according to claim 1, wherein after the step of performing a subsequent adjustment of power, the method further comprises the steps of:
   determining a third average impedance during a third sample window;
   determining a fourth average impedance during a fourth sample window; and
   applying the electrosurgical waveform for a fifth sample window if the third and fourth average impedance are substantially equal.

6. A method for controlling an electrosurgical waveform generated by an electrosurgical generator comprising the steps of:
   activating an electrosurgical generator to produce an electrosurgical waveform;
   increasing power of the electrosurgical waveform during a first sample window of a normal priority task;
   determining a direction of change in a first average impedance during the first sample window of the normal priority task in response to the increase in power of the electrosurgical waveform;
   performing a first adjustment of power of the electrosurgical waveform in response to the direction of change in the first average impedance during a subsequent sample window of the normal priority task;
   determining a direction of change in a subsequent average impedance during the subsequent sample window of the normal priority task in response to the first adjustment of power; and
   performing a subsequent adjustment of power of the electrosurgical waveform in response to the direction of change in the subsequent average impedance, wherein the subsequent adjustment of power is reverse to that of the first adjustment of power when the direction of change in the first and subsequent average impedances is the same.

7. A method according to claim 6, wherein after the step of activating an electrosurgical generator to produce an electrosurgical waveform, the method further comprises the steps of:
   continuously measuring peak impedance during a first sample window of a high priority task, wherein the high priority task is layered over the normal priority task and configured to operate concurrently therewith; and comparing the peak impedance to a predetermined threshold change in impedance to determine a rapid rise in impedance.

8. A method according to claim 6, wherein after the step of activating an electrosurgical generator to produce an electrosurgical waveform, the method further comprises the steps of:

determining a first average impedance during a first sample window of a low priority task, wherein the low priority task is layered over the normal priority task and configured to operate concurrently therewith;

determining a second average impedance during a second sample window of the low priority task; and applying the electrosurgical waveform for a third sample window of the low priority task if the third and fourth average impedance are substantially equal.

9. A control system for use with an electrosurgical generator adapted to generate an electrosurgical waveform for application to tissue comprising:

a controller configured to adjust power of an electrosurgical waveform generated by an electrosurgical generator, wherein the controller increases power of the electrosurgical waveform during a first sample window;

a sensor module configured to continually sense tissue impedance resulting from the application of the electrosurgical waveform to the tissue and generate at least one signal relating thereto; and at least one loop control module in operative communication with the controller for receiving the at least one signal from the sensor module to determine a direction of change in a first average impedance during the first sample window in response to the increase in power of the electrosurgical waveform made by the controller, wherein the controller performs a first adjustment of power of the electrosurgical waveform in response to the direction of change in the first average impedance during a subsequent sample window;

wherein the at least one loop control module is further configured to determine a direction of change in a subsequent average impedance during the subsequent sample window in response to the first adjustment of power made by the controller; and wherein the controller is further configured to perform a subsequent adjustment of power of the electrosurgical waveform in response to the direction of change in the subsequent average impedance, wherein the subsequent adjustment of power is reverse to that of the first adjustment of power when the direction of change in the first and subsequent average impedances is the same.

10. A control system according to claim 9, further comprising:

a plurality of impedance filters configured to receive the at least one signal generated by the sensor module and filter at least one of the first average impedance and the subsequent average impedance and generate at least one signal relating thereto for transmitting to the controller.

11. A control system according to claim 9, further comprising:

a user interface in bidirectional communication with the controller which allows a user to select at least one pre-surgical parameter, the at least one pre-surgical parameter including at least one of a level of increase of power of the electrosurgical waveform during the first sample window, a level of the first adjustment of power of the electrosurgical waveform during the subsequent sample window, and a level of the subsequent adjustment of power of the electrosurgical waveform.

12. A control system according to claim 9, wherein the controller is further configured to increase the power of the electrosurgical waveform in response to a decrease in the first average impedance and decrease the power of the electrosurgical waveform in response to an increase in the first average impedance.

13. A control system according to claim 9, wherein the controller is further configured to decrease the power of the electrosurgical waveform in response to a decrease in the first average impedance and increase the power of the electrosurgical waveform in response to an increase in the first average impedance.

14. A control system according to claim 9, wherein the sensor module is configured to continuously measure a peak impedance during a third sample window and generate at least one signal relating thereto and wherein the at least one loop control module is configured to receive the at least one signal relating to the peak impedance from the sensor module to compare the peak impedance to a predetermined threshold change in impedance to determine a rapid rise in impedance.

15. A control system according to claim 9, wherein the sensor module is further configured to determine a third average impedance during a third sample window and determine a fourth average impedance during a fourth sample window and wherein the controller applies the electrosurgical waveform for a fifth sample window if the third and fourth average impedance are substantially equal.

* * * * *